United States Patent [19]

Krug et al.

[11] Patent Number: 5,974,111

[45] Date of Patent: *Oct. 26, 1999

[54] IDENTIFYING EXPLOSIVES OR OTHER CONTRABAND BY EMPLOYING TRANSMITTED OR SCATTERED X-RAYS

[75] Inventors: Kristoph D. Krug, Framingham; William F. Aitkenhead, Sharon; Richard F. Eilbert, Lincoln, all of Mass.; Jeffrey H. Stillson, Nashua, N.H.; Jay A. Stein, Framingham, Mass.

[73] Assignee: Vivid Technologies, Inc., Woburn, Mass.

[*] Notice: This patent is subject to a terminal disclaimer.

[21] Appl. No.: 08/849,275

[22] PCT Filed: Sep. 24, 1996

[86] PCT No.: PCT/US96/15260

§ 371 Date: Dec. 5, 1997

§ 102(e) Date: Dec. 5, 1997

[87] PCT Pub. No.: WO97/12228

PCT Pub. Date: Apr. 3, 1997

[51] Int. Cl.[6] .................................................. G01N 23/10
[52] U.S. Cl. ................................ 378/57; 378/53; 378/90
[58] Field of Search .................................. 378/51, 53, 54, 378/56, 57, 62, 63, 86, 87, 88, 89, 90, 207

[56] References Cited

U.S. PATENT DOCUMENTS

| | | | |
|---|---|---|---|
| 4,799,247 | 1/1989 | Annis et al. | 378/87 |
| 4,839,913 | 6/1989 | Annis et al. | 378/44 |
| 4,864,142 | 9/1989 | Gomberg | 250/390.04 |
| 4,884,289 | 11/1989 | Glockmann et al. | 378/57 |
| 4,974,247 | 11/1990 | Friddell | 378/90 |
| 5,007,072 | 4/1991 | Jenkins et al. | 378/88 |
| 5,022,062 | 6/1991 | Annis | 378/86 |
| 5,044,002 | 8/1991 | Stein | 378/54 |
| 5,091,924 | 2/1992 | Bermbach et al. | 378/57 |
| 5,179,581 | 1/1993 | Annis | 378/57 |
| 5,182,764 | 1/1993 | Peschmann et al. | 378/57 |
| 5,224,144 | 6/1993 | Annis | 378/146 |
| 5,247,561 | 9/1993 | Kotowski | 378/87 |
| 5,253,283 | 10/1993 | Annis et al. | 378/100 |
| 5,260,981 | 11/1993 | Uyama | 378/57 |
| 5,260,982 | 11/1993 | Fujii et al. | 378/87 |
| 5,319,547 | 6/1994 | Krug et al. | 364/409 |
| 5,394,454 | 2/1995 | Harding | 378/86 |
| 5,428,657 | 6/1995 | Papanicolopoulos et al. | 378/86 |

FOREIGN PATENT DOCUMENTS

| | | | |
|---|---|---|---|
| 0 271 723 | 11/1987 | European Pat. Off. | G01V 5/00 |
| 42-10-156-A1 | 10/1993 | Germany . | |

*Primary Examiner*—David P. Porta
*Attorney, Agent, or Firm*—Fish & Richardson P.C.

[57] ABSTRACT

An X-ray inspection device (10) for detecting a specific material of interest in items of various sizes and shapes (24A, 24B, 24C) includes an X-ray source system located at an inspection region and constructed to expose the examined item to at least one beam of X-ray radiation, and one or more X-ray detection systems (60, 80, 100). The X-ray inspection device also includes one or more dimension detectors (120) constructed to measure a selected dimension of the examined item, an interface system connected to receive X-ray data and dimension data, and a computer programmed to utilize the data for recognition of the specific material of interest and to indicate its presence in the examined item. Each detection system includes one or more arrays of X-ray detectors arranged in a linear, circular or semi-spherical geometry.

3 Claims, 15 Drawing Sheets

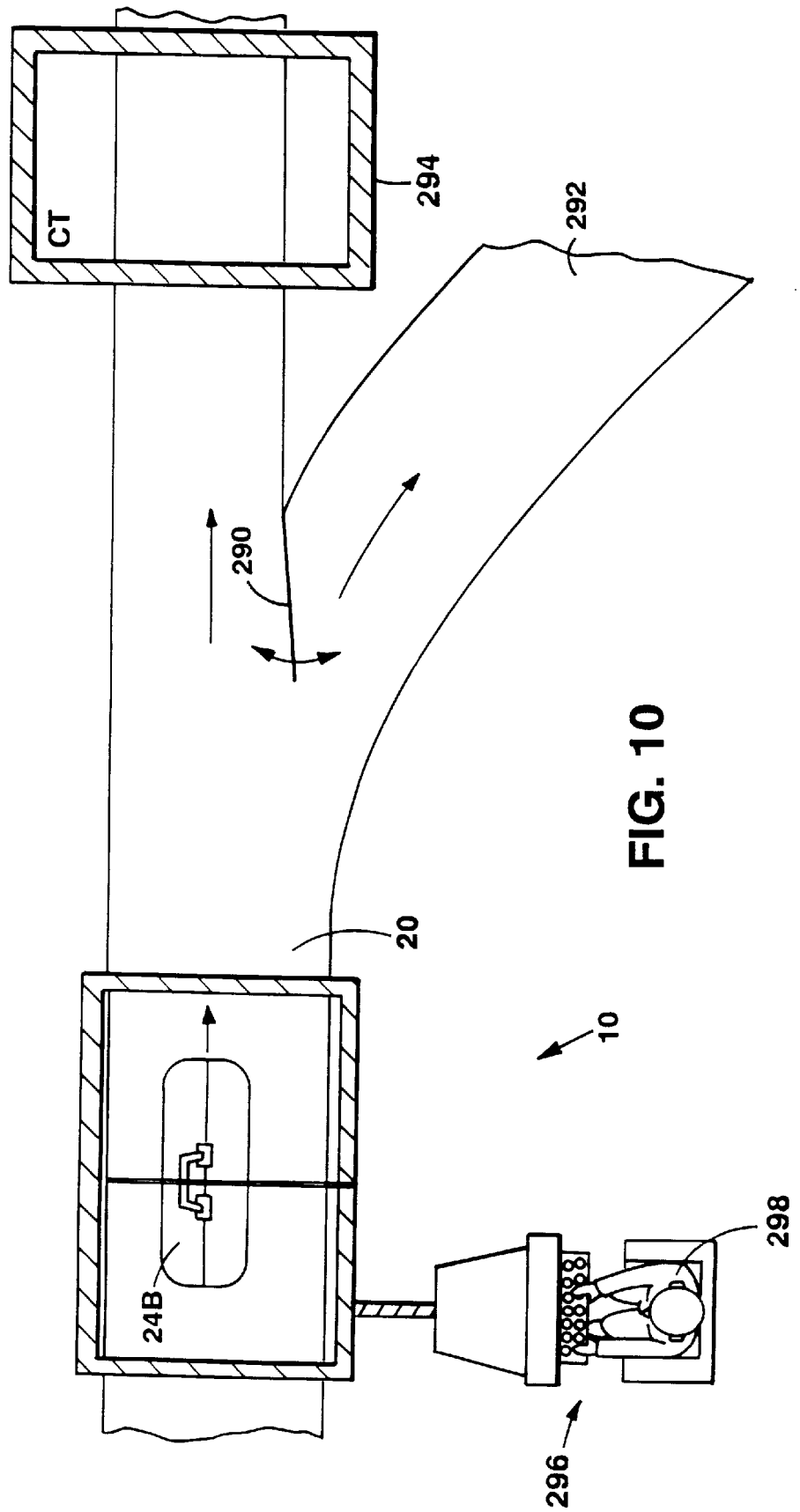

IDENTIFYING EXPLOSIVES OR OTHER CONTRABAND BY EMPLOYING TRANSMITTED OR SCATTERED X-RAYS

The present invention relates to X-ray inspection systems for examination of packages or baggage. More specifically, the invention concerns systems that utilize X-ray radiation transmitted through or scattered from the examined package or baggage to detect weapons, explosives or other contraband.

BACKGROUND OF THE INVENTION

Over the past several years, X-ray baggage inspection systems have evolved from simple X-ray imaging systems that were completely dependent on interpretation by an operator to more sophisticated automatic systems that can automatically recognize certain types of contraband. The more sophisticated inspection systems have employed single energy or dual energy X-ray radiation transmitted through the examined baggage. Some systems have used a single view source detector arrangement, others have utilized a dual view or multi-view arrangements. The single or dual view systems usually scan baggage, as it moves on a conveyor, using a fan beam or a scanning pencil beam of X-rays to provide projection images. The multiview, CT type systems generally scan stationary baggage and process data corresponding to absorption of X-rays to reconstruct a cross-sectional view of the contents of the baggage. These systems usually display their decision by highlighting objects or regions in the examined baggage in different colors.

The dual energy inspection systems may also use the ratio of the attenuation values at the two energies to discriminate between low Z materials (e.g., plastics) and high Z materials (e.g., metals). However, many inspection systems cannot distinguish contraband when covered by a high density material, such as a sheet of metal.

To locate a low density material in baggage, some inspection systems employ both transmitted and scattered radiation. Such systems use an X-ray source located on one side of an inspection region and a detector located on the other side of the inspection region. The X-ray source emits a fan beam or a scanning pencil beam of X-rays that are transmitted through the examined baggage and detected by the detector. These systems may also employ an X-ray forward-scatter detector disposed near the X-ray transmission detector to detect photons scattered by the illuminated object out of the path of the transmitted beam. A back-scatter detector is usually disposed on the same side as the X-ray source and detects photons back-scattered out of the beam path by the object. The systems may display a transmission image and both scatter images for an operator, who then decides whether contraband is located in the baggage based on the shape and location of the imaged items. These systems may also digitally manipulate the scatter image and produce a selected parameter associated with a particular contraband, e.g., a histogram that is then compared to a predetermined characteristic of the probed contraband. The systems can also sound an alarm if the contraband is detected.

In general, many X-ray transmission systems are not able to effectively detect low Z materials (such as plastics or plastic explosives), especially when shaped into objects of thin cross-section, since they cause relatively small attenuation of X-rays. On the other hand, some X-ray scatter systems are not able to consistently identify weapons, explosives or drugs located deep inside baggage. Some X-ray systems have too low a throughput for use as an in-line inspection device at the airport. There is a need for a high speed X-ray inspection device that can reliably detect weapons, various explosives (or other contraband) having different shapes and sizes and being located anywhere in the examined baggage.

SUMMARY OF THE INVENTION

In general, the X-ray inspection system detects different types of contraband (for example, weapons, drugs, money, plastic explosives like C4, RDX, Semtex, Seismoplast, PE4 or other explosives like TNT, dynamite, 4MX, PETN, ANFO) that may be present in baggage by detecting both X-ray radiation transmitted through and scattered from the baggage.

An X-ray inspection device for detecting a specific material of interest (typically contraband) in items of various sizes and shapes includes an X-ray source system located at an inspection region and constructed to expose the examined item to a beam of X-ray radiation, an x-ray detection system located at the inspection region and constructed to detect X-ray radiation modified by the examined item. The X-ray inspection device also includes a dimension detector constructed to measure a selected dimension of the examined item, an interface system connected to and receiving from the X-ray detection system X-ray data and from the dimension detector dimension data, the interface system being constructed to order the X-ray data and the dimension data, and a computer operatively connected to and receiving from the interface system the ordered X-ray and dimension data. The computer is programmed to utilize the data for recognition of a specific material of interest in the examined item and to indicate its presence in the examined item.

The X-ray inspection device includes one or more dimension detectors located at different positions at or near the inspection region. The invention envisions different types of dimension detectors that utilize optical radiation in the UV to IR range or ultrasound. Alternatively, the dimension detector may use a mechanical sensor that measures a location or a selected dimension of the examined item.

In one embodiment, the dimension detector includes an optical source, an optical detector, and a processor. The optical source, located near the inspection region, is constructed to emit optical radiation in the ultraviolet to infrared range toward the examined item. The optical detector, located near the inspection region, is constructed to detect optical radiation that may be partially modified by the examined item. The processor, connected to receive optical data from the optical detector, is constructed to measure the selected dimension of the examined item.

In another embodiment, the dimension detector includes an ultrasonic transducer, located near the inspection region, constructed to emit ultrasonic waves toward the examined item and detect ultrasonic waves reflected from the examined item, from the conveyor or another surface at the inspection region. This dimension detector also includes a processor connected to receive ultrasonic data from the ultrasonic transducer and constructed to measure the selected dimension of the examined item.

The X-ray inspection device includes one or more X-ray source systems. The X-ray source system emits pulses of a fan beam of X-ray radiation of one energy, or of at least two substantially different energies. The device may use two X-ray source systems emitting two discrete fan beams spaced apart by a fixed distance. These fan beams may be directed to the examined item at the same angle or may utilize different angles of inspection. Alternatively, the X-ray source system may use one or more scanning X-ray pencil beams.

The X-ray inspection device includes several X-ray detection systems that detect transmitted and/or scattered X-ray radiation utilizing several different geometries. The scattered radiation can identify contraband that does not usually carry any particular shape and attenuates only slightly the transmitted radiation due to its configuration, low density, or low atomic number Z. There may be one or more X-ray back-scatter detection systems, and one or more X-ray forward-scatter detection systems detecting X-ray radiation scattered at different angles from different surfaces of the examined item. Each detection system includes one or more arrays of X-ray detectors arranged in a linear, circular or semi-spherical geometry. Each detection system also may be connected to a displacement unit constructed and arranged to move or rotate the detector array to a selected position relative to the inspection region and the examined item.

The X-ray inspection device includes a display, operatively connected to the computer, constructed and arranged to display a selected image of data representing a select region of the item. The image is created from the X-ray transmission data, the X-ray back-scatter data or the X-ray forward-scatter data, or based on their combination. The image can also be created based on a selected signature of a specific material of interest; his signature is calculated using the X-ray transmission data, the X-ray back-scatter data or the X-ray forward-scatter data, and the dimension data. The X-ray inspection device may also include a user interface, operatively connected to the computer, constructed and arranged to enable an operator to obtain different images of the region of the examined item. The user interface also enables an operator to interact with the recognition process and make an additional decision about the presence of the specific material of interest in the examined item.

The X-ray inspection device is a precision X-ray transmission and scatter detection setup that aligns the scattered radiation images with the transmission image using a fan beam geometry and a unique collimation. This collimation allows the data from the various detection arrays to be processed and compared on a region-by-region basis. The device performs a series of autocalibration and normalization sequences to produce normalized data sets, and also equalizes the scattered data relative to the transmitted attenuation data to obtain equalized scatter data that possess intrinsic material information. The normalization and equalization sequences employ dimension data provided by one or more dimension detectors. Then, the device uses this spatially correlated and equalized precision data to automatically detect threat objects such as thin sheets of explosives or contraband arranged in various configurations and hidden in baggage or other items used by terrorists or smugglers. The dimension detector data is also useful in the evaluation of the transmission radiation data by itself, for example, to improve accuracy of mass and density estimation of these objects. The mass and density information then serves to lower the false alarm rate and improve threat detection.

BRIEF DESCRIPTION OF THE DRAWINGS

FIG. 10 shows schematically the X-ray baggage inspection device including a work station and a separate CT scanner for further inspection.

DESCRIPTION OF THE PREFERRED EMBODIMENTS

Figure 1:
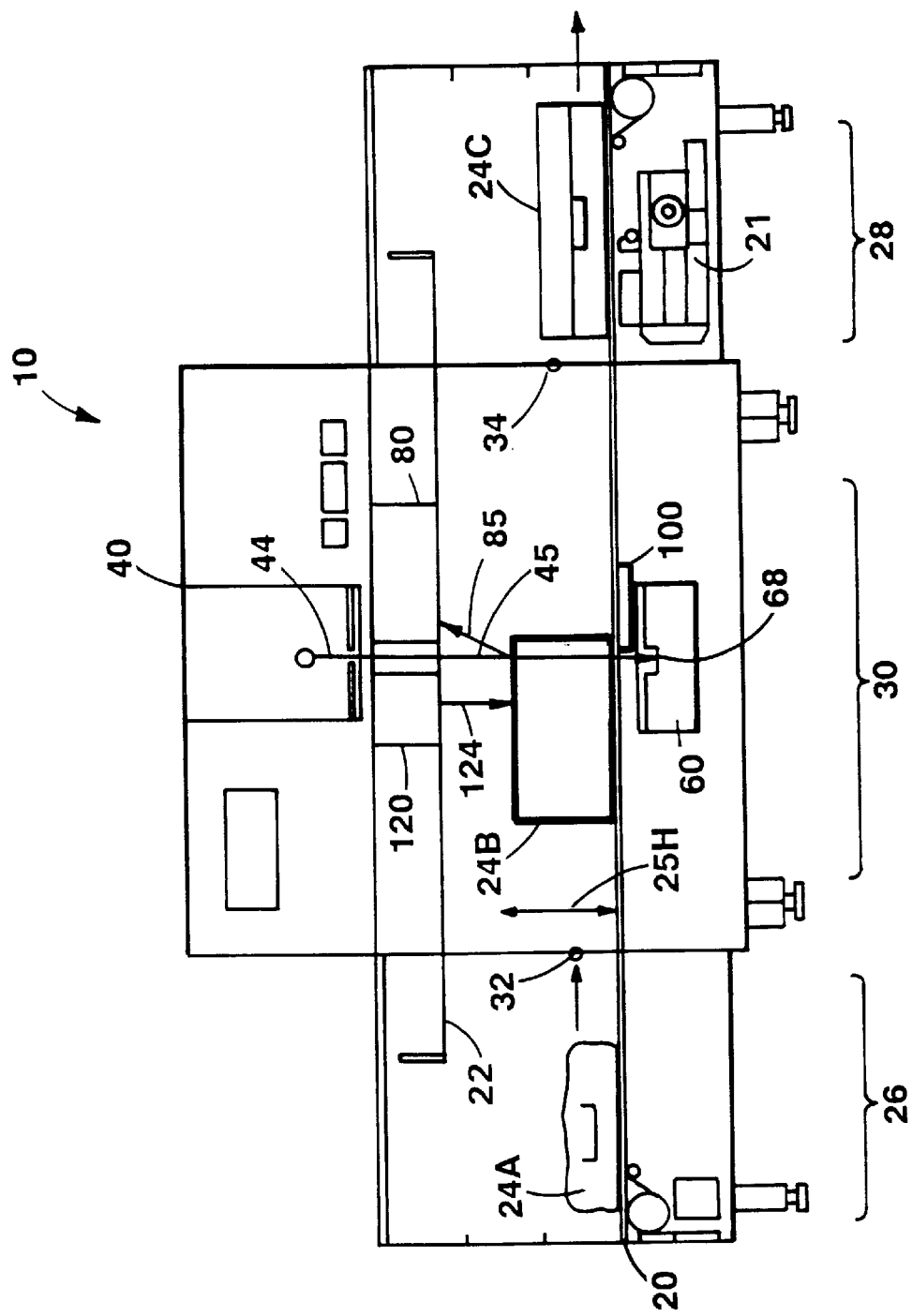
FIG. 1 is a schematic side view of an X-ray baggage inspection device.

Referring to FIG. 1, an X-ray inspection system 10 includes a conveyor 20, driven by a motor 21, constructed to transport items of baggage or packages (24A, 24B, 24C ... ) from a loading region 26 through an inspection region to an unloading region 28. Inspection region includes a set of photocells 32, an X-ray source system 40, three X-ray detector systems 60, 80 and 100, and a dimension detector 120. Items of baggage 24A, 24B, 24C have the maximum height of 457 mm, to fit between the conveyor surface and a restricting plate 22, and the maximum width of 1016 mm. (Another embodiment of the inspection system is disclosed in detail in U.S. Pat. No. 5,319,547 which is incorporated by reference as if fully set forth herein.)

Inspection system 10 also includes a data interface system and a computer system, all of which will be described in detail in connection with FIG. 7. The computer system includes a VME-based 80386 host computer linked to a network of "super-micro" I860 based computers with the architecture configured for expandable parallel data processing in a Multiple-Instruction Multiple Data (MIMD) configuration. The processed data is sent via the VME bus to an intelligent graphics card that includes a TMS34020 graphics processor. The image data is displayed on a 1024×1280 pixel, high resolution monitor.

Photocells 32, located at the entrance to inspection region 30, sense entry of an item of baggage or package and send a control signal to the computer system via the data interface system. The computer activates dimension detector 120, which registers the height (25H) of examined baggage 24B and may also detect its width (25W) and length (25L). The computer system also activates the X-ray source system 40, which emits pulsed, dual energy X-rays 44, colimated into a fan beam of X-ray radiation 45, which strikes examined baggage 24B. The transmitted X-ray radiation is detected by transmission detector 60, X-ray radiation scattered from the top layers of baggage 24B is detected by back-scatter detector 80, and X-ray radiation scattered from the bottom layers of baggage 24B is detected by forward-scatter detector 100.

Figure 1A:
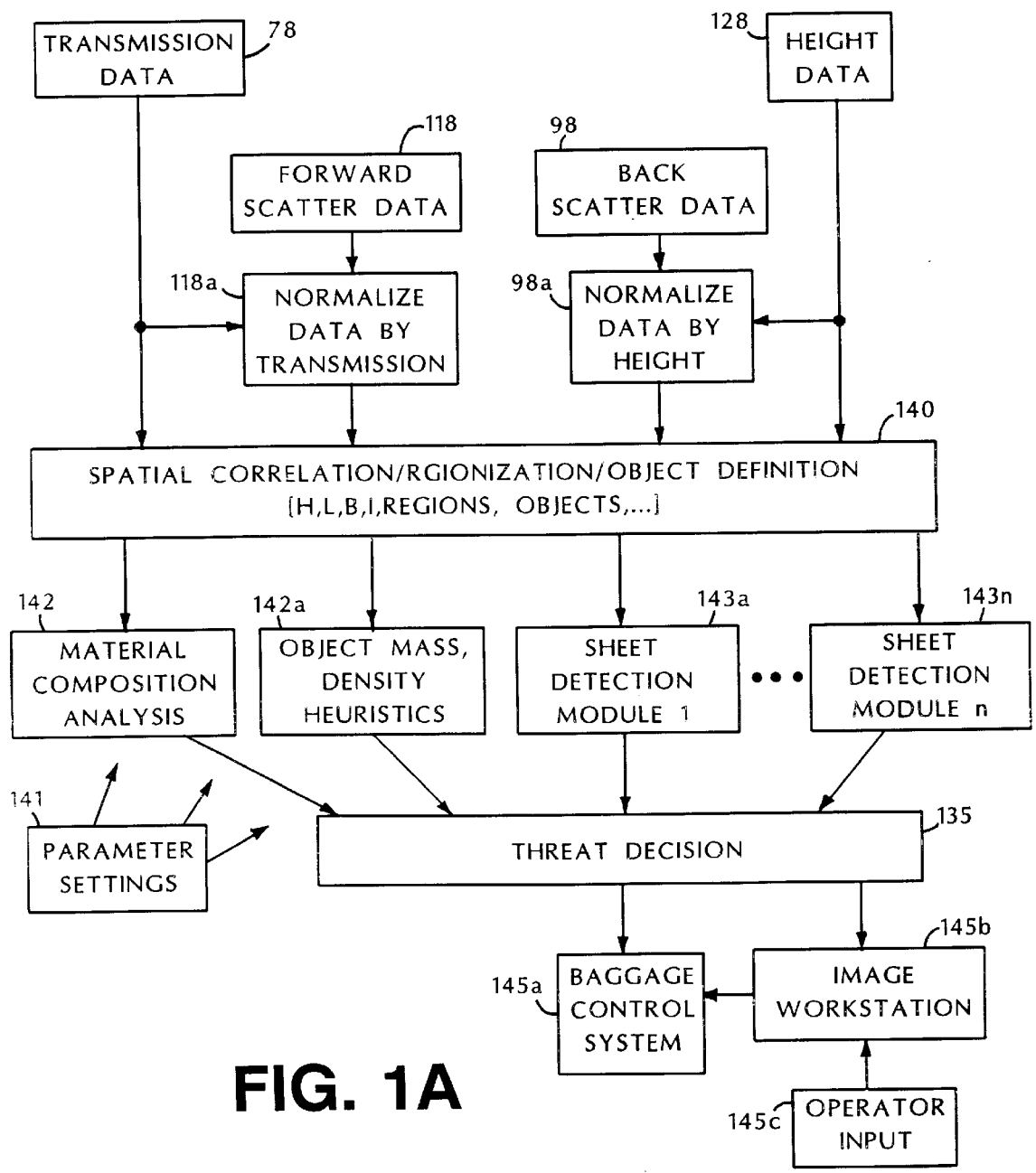
FIG. 1A shows diagrammatically the overall architecture of the detection algorithm.

Referring to FIG. 1A, in general, the recognition algorithms utilize digitized transmission data 78, back-scatter data 98, forward-scatter data 118, and height data 128. The various algorithms use these sources of data in different combinations to detect explosives and explosive devices or contraband in a variety of targeted configurations.

Figure 2:
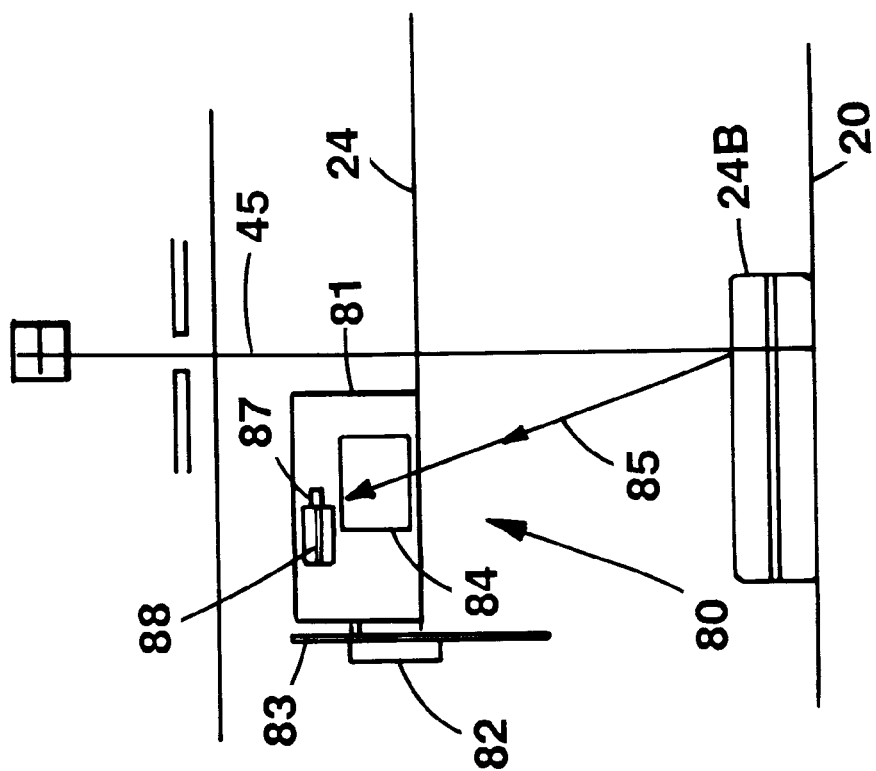
FIGS. 2 and 2A show schematic views of a back-scatter detector employed in the device of FIG. 1.
Figure 2A:
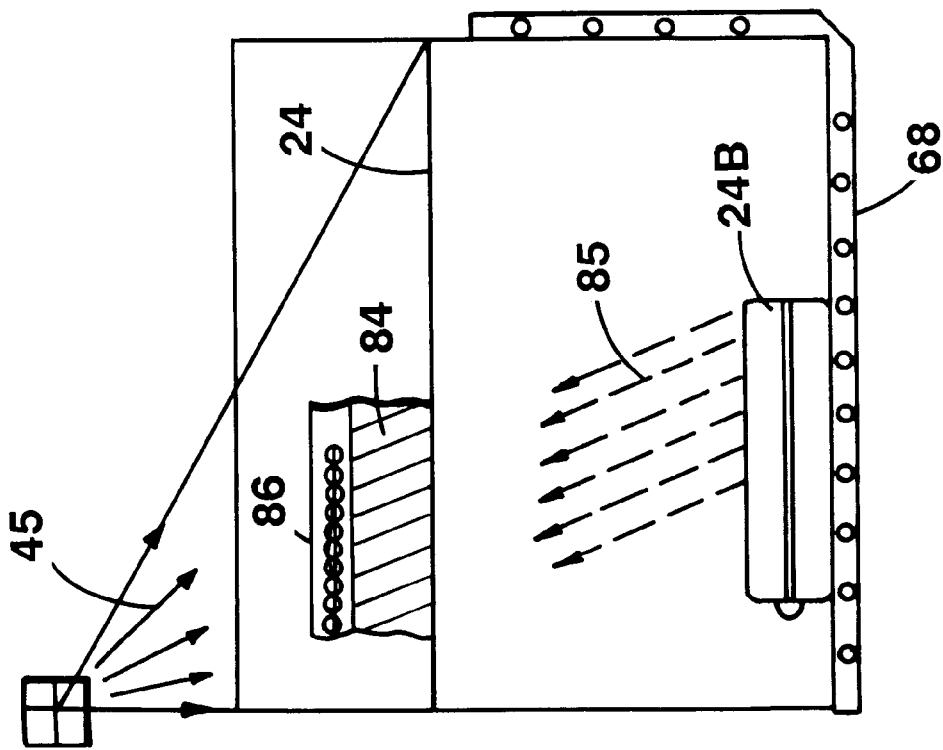

Referring to FIGS. 2 and 2A, back-scatter detector 80 includes a collimator 84, an array of 21 X-ray detectors 86 and the corresponding electronics. Back-scatter detector 80 is located in a shielded box 81 mounted just out of the plane of X-ray fan beam 45. Box 81 is mounted on the trailing side of fan beam 45 directly above the conveyor part that is exiting fan beam 45. Collimator 84 is fabricated of a thin, dense material (e.g., lead, tin, copper) and is designed to have a high collimation ratio. Collimator 84 defines the view of each detector 86; this view parallels the view of X-ray transmission detector 68 (described below). Although X-ray radiation is scattered in all directions, each X-ray detector 86 receives radiation 85 back-scattered primarily from the top parts of irradiated baggage 24B. Furthermore, the Compton radiation detected by back-scatter detector 86 can be correlated by location and orientation to the X-ray attenuation data detected by transmission detector 60.

Figure 2B:
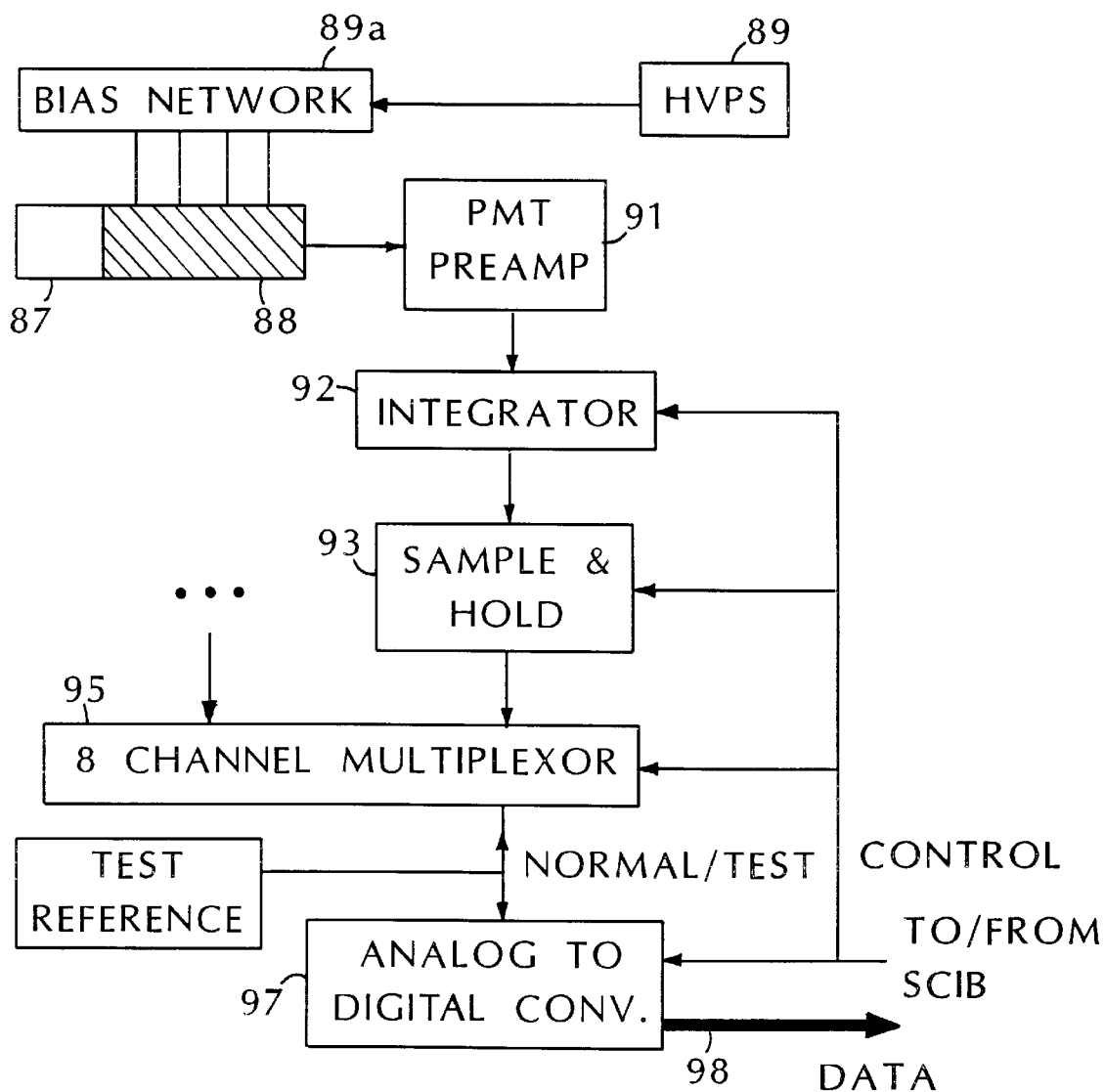
FIG. 2B shows diagrammatically electronics of the scatter detector.

Also referring to FIG. 2B, each back-scatter X-ray detector 86 includes an NaI crystal 87 (or other scintillating crystal, screen or paper) located at the detection window of a photomultiplier tube (PMT) 88 connected to a high voltage bias network (89a) and a power supply 89. Power supply 89 is a DC-DC converter type supply. Mounted within box 81 and connected to each PMT 88 is conditioning, amplifying and processing circuitry. The circuitry includes a preamplifier 91, an integrator 92, a sample and hold circuit 93, a multiplexer 95, and an analog to digital converter 97. Back-scattered X-ray radiation 85 excites in crystal 87 visible light that is detected by PMT 88. The detector signal is amplified by preamplifier 91 and integrated over a selected collection time by integrator 92. A sample and hold circuit 93 keeps the integrated signal until it is read by an eight channel multiplexer 95, which receives detector signals from seven detectors. After the processed analog signal is digitized by analog-to-digital converter 97, digitized data 98 are sent to the scatter interface board (SCIB).

In an alternative embodiment, a displacement unit 82 may be attached to box 81. Displacement unit 82 moves detector 80 to a selected position relative to the inspection region and baggage 24B. The displacement unit includes a servo assembly, responsive to signals from dimension detector 120, which moves box 81 on a track 83. By moving scatter detector 80 to a selected location, the scatter detector data are compensated for the varying distance from the surface of baggage 24B to detector array 86. This compensation increases signal to noise in the scatted data and thus improves detection probability of threat objects in baggage of different sizes.

Figure 3:
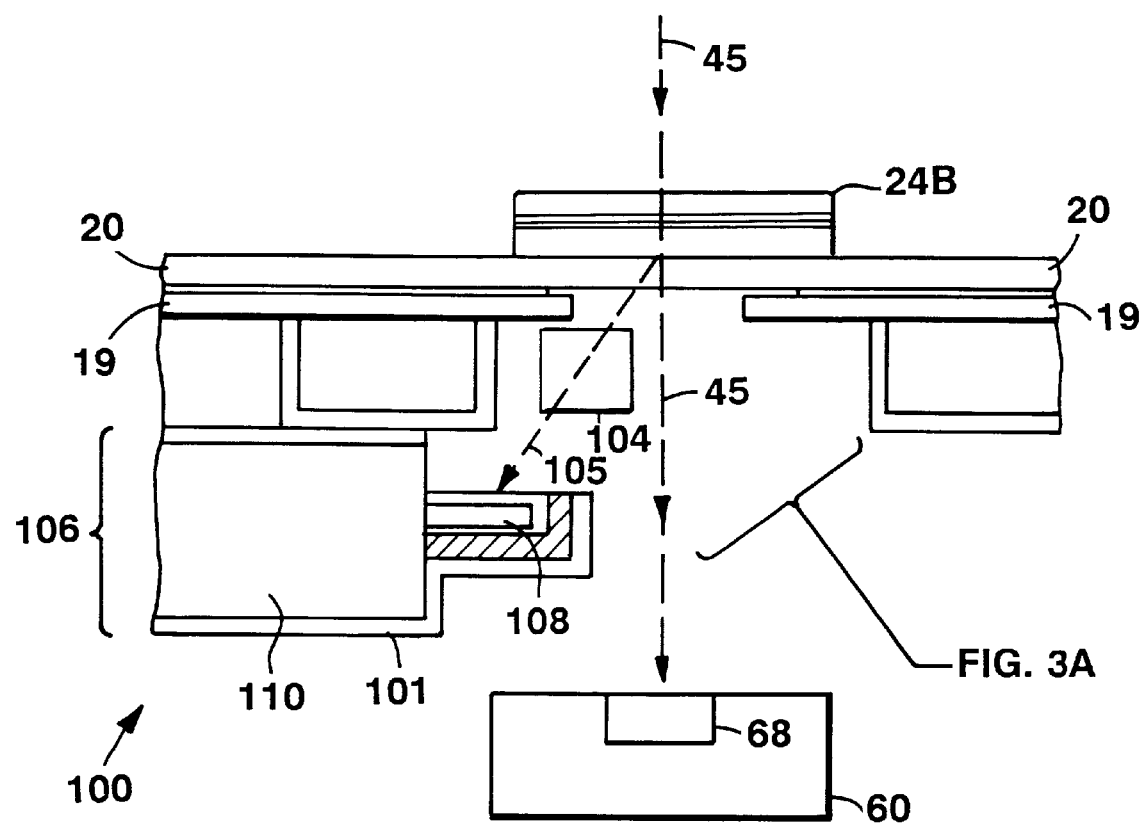
FIGS. 3 and 3A show schematic side views of a forward scatter detector employed in the device of FIG. 1.
Figure 3A:
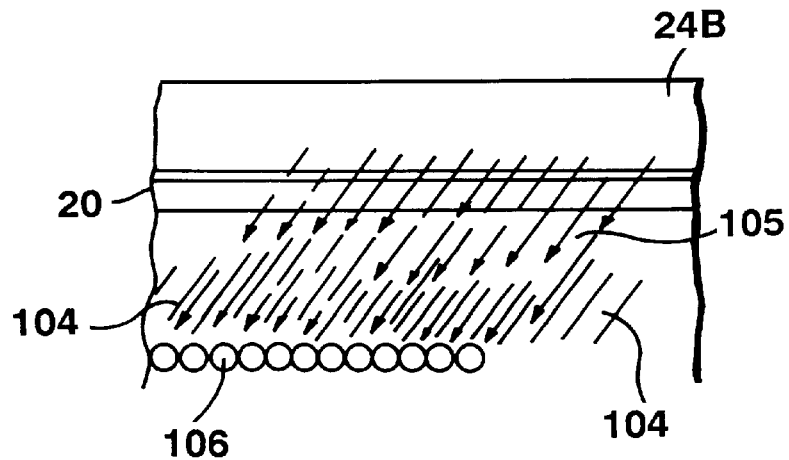

Referring to FIG. 3, forward-scatter detector 100 includes a collimator 104, an array of 28 X-ray detectors 106 and the corresponding electronics. Forward-scatter detector 100 is located in a shielded box 101 mounted below deck 19 just out of the plane of X-ray fan beam 45 and just above transmission detector 60. Most of the X-ray radiation arriving at the bottom of baggage 24B is transmitted directly to detector 60, but a portion of the radiation is scattered in all directions. Also referring to FIG. 3A, collimator 104 is constructed to set the view of each X-ray detector 106 so that it receives X-rays 105 scattered from the first 2 cm to 3 cm of the bottom surface of baggage 24B. Furthermore, collimator 104 sets the view of each detector 106 to parallel the view of a selected number of X-ray transmission detectors 68. Thus the locations observed by detector array 106 can be spatially correlated to the locations observed by main detector array 68. Each X-ray detector 106 includes a $CdWO_4$ crystal 108 (or other scintillating crystal or paper) located at the detection window of a photomultiplier tube (PMT) 110 connected to a high voltage power supply 112. Forward-scatter detector array 106 uses electronics similar to the electronics of back-scatter detector array 86, shown in FIG. 2B.

Figure 4:
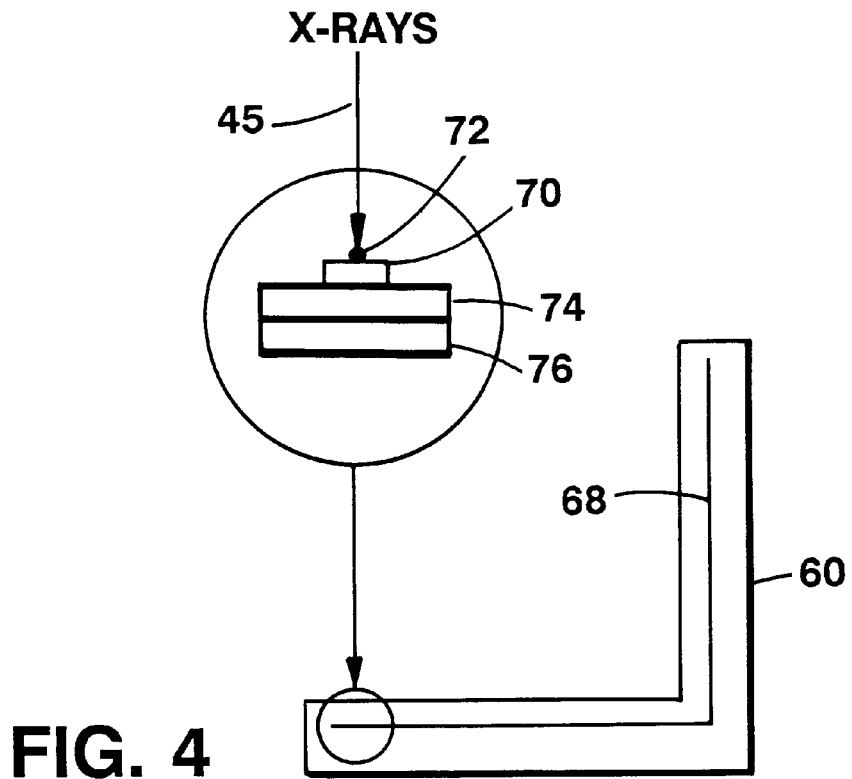
FIG. 4 shows schematically a transmission detector employed in the device of FIG. 1.

Referring to FIG. 4, X-ray transmission detector 60 includes L-shaped array 68 of 960 detectors designed to detect X-ray fan beam 45 at high and low energy bands transmitted through baggage 24B. Each detector includes a large area photodiode 70 with a scintillating material 72 glued over its active area with an optically transparent epoxy. Similarly as for the scatter detectors, when array 68 is exposed to X-ray radiation, the scintillating material converts some of the X-rays to visible photons, which are then detected by photodiodes 70 and converted to small electric currents. This signal is amplified by a preamplifier 74 and the output is sent to a multiplexer 76. The multiplexer distributes 8 signals at a time via eight analog busses to an analog-to-digital (A/D) conversion board 77 (FIG. 7).

Figure 7:
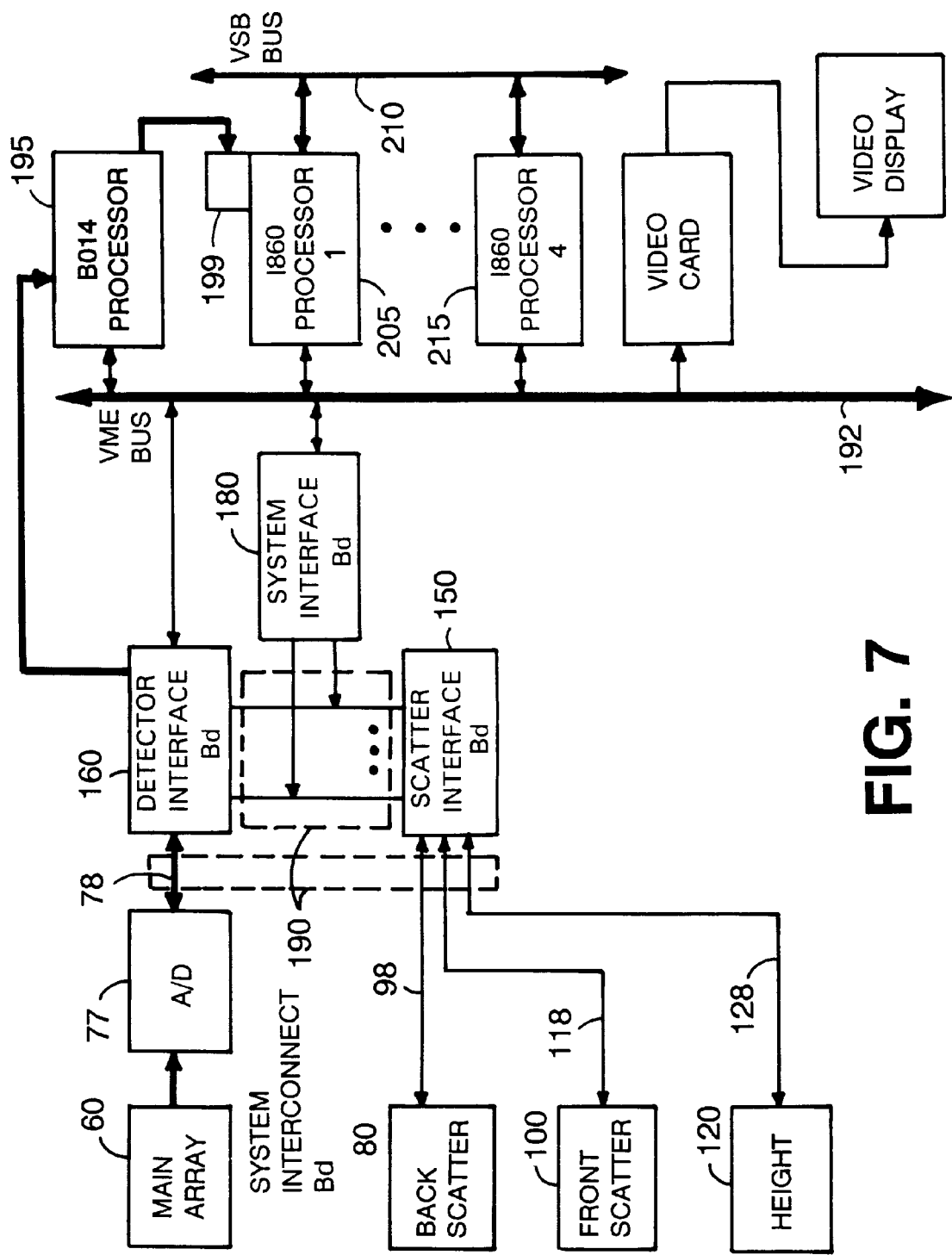
FIG. 7 is a block diagram displaying hardware and data organization of the device of FIG. 1.

Transmission detector 60 provides to a detector interface board (DIB) 160 of FIG. 7, a digitized stream of values (78) representing the high and low X-ray band detection values, and optionally "dark current" values (which also include after-glow of the scintillator) for each detector per pulse of X-rays. The DIB board can perform dark current subtraction to produce dark current corrected high (H) and low (L) X-ray data. Similarly, the SCIB board can produce dark current corrected high (H) and low (L) X-ray scatter data detected by forward-scatter detector and back-scatter detector.

Figure 5:
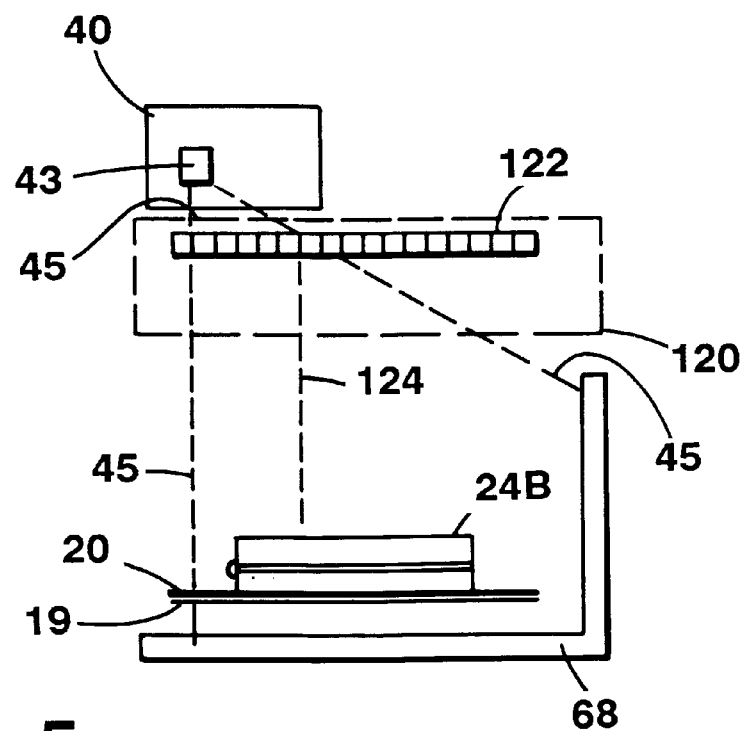
FIGS. 5 and 5A show schematically a dimension detector employed in the device of FIG. 1.
Figure 5A:
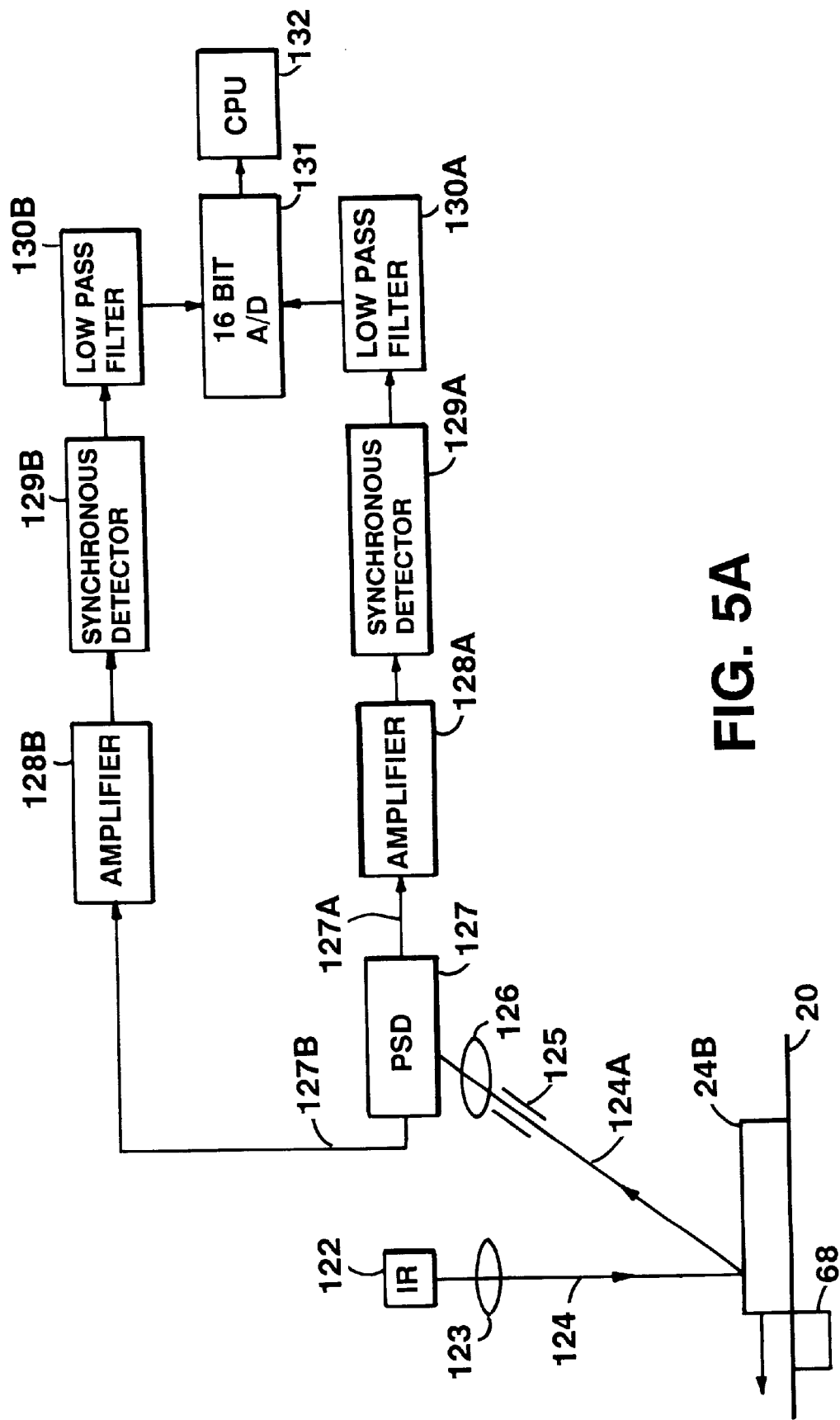

Referring to FIGS. 5 and 5A, dimension detector 120 is an optical detector that includes an array of 40 IR light emitting diodes (LEDs) 122 and of 40 corresponding position sensitive diodes (PSDs) 127; the array operates as follows. Each LED 122 emits a pulsed IR beam 124, at a constant frequency, which passes through a focusing lens 123 and irradiates the top surface of conveyer 20 or baggage 24B. The reflected IR light (124a) is focused by a lens 126 and detected by PSD 127. An optical collimator 125 may be used to reduce the cross-talk between the individual LEDs. PSD 127 outputs analog voltage signals Va (127A) and Vb (127B) corresponding to a location of the beam on its surface. In a differential detection scheme, the voltage signals are amplified (128A, 128B) and detected synchronously (129A, 129B) to the "on" pulse time of the LEDs. The output of the detection stage is then low-pass filtered (130A, 130B) and presented to an analog-to-digital converter 131 by way of a signal demultiplexor.

These signals represent the total optical power received by the PSD and the position of the focused light beam along the length of the PSD. The ratio of each channel's signal to the sum total of both channels represents the position of the center of the light energy relative to the active area of the PSD. The distance data is calculated by triangulation by a processor as follows:

$$\text{Distance} = \frac{K_1}{\frac{(Va - Vb - Za + Zb)}{(Va + Vb - Za - Zb)} K_2 + K_3} + K_4$$

wherein $K_1$ is a horizontal distance of detector lens 126 to LED 122 times the vertical distance of lens 126 to PSD 127;

$K_2$ is a PSD position conversion constant;

$K_3$ is a midpoint constant when Va−Vb−Za+Zb=0;

$K_4$ is a distance of the detector lens to the measurement 0 point;

Za=ZLEDa+ZADa is a detector channel A zero output;

Zb=ZLEDb+ZaDb is a detector channel B zero output;

and Va and Vb are output voltages from the PSD.

Figure 5B:
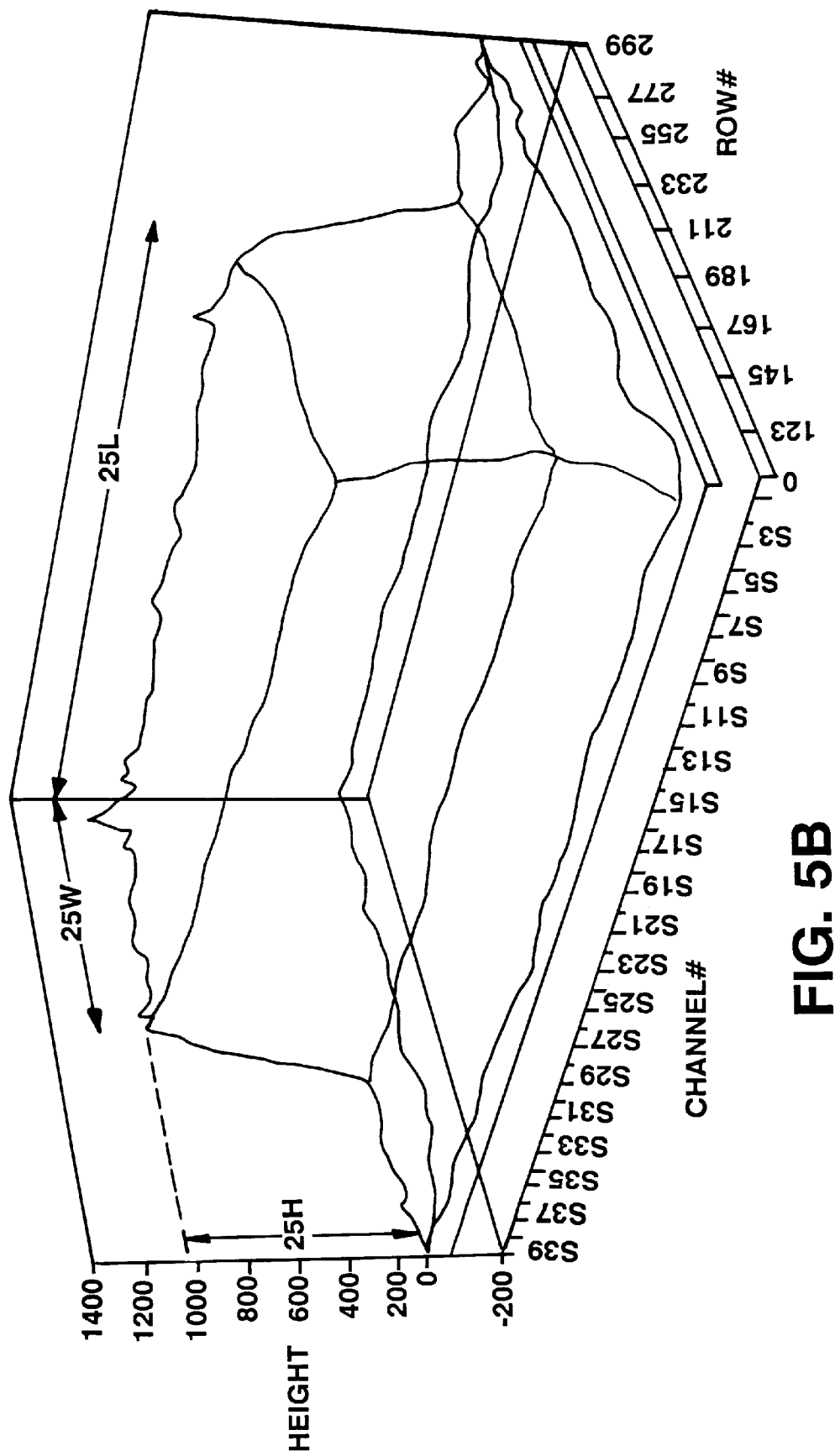
FIG. 5B shows height data of a package measured by the dimension detector of FIG. 4.

As baggage 24B moves on conveyor 20, dimension detector 120 collects for each pixel the distance data. As the distance between the conveyor surface and each laser diode is known, a processor can re-calculate the detected data to obtain the height data of baggage 24B. The height data (i.e., surface topology) of the moving baggage measured by dimension detector 120 are shown in FIG. 5B. The height resolution of dimension detector 120 is about 1 cm to 2 cm. If a pixel returns an abnormal value or a "no data" value, the system estimates the missing value by averaging the data of the surrounding pixels.

Since the items to be inspected are of varying heights and sizes, the scatter radiation detector efficiencies are a strong function of distance from the scatter target to the scatter detector. The dimension detector provides the distance data used to normalize the scatter detector data to be compensated for the varying distance from the surface of the examined baggage. The normalization improves detection probability of threat objects in baggage of different sizes.

Figure 6:
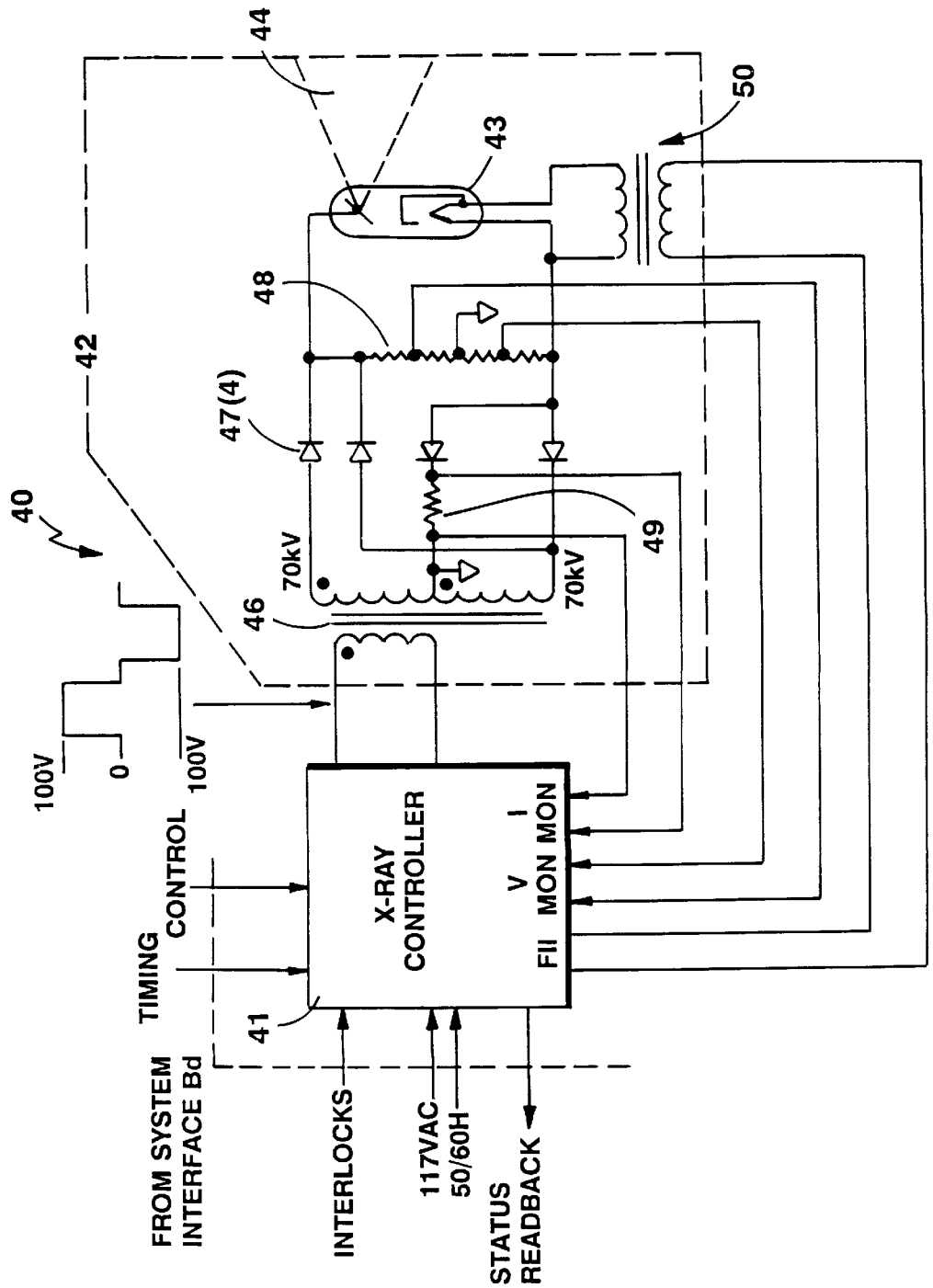
FIG. 6 is a circuit diagram of an X-ray source employed in the device of FIG. 1.

Referring to FIG. 6, X-ray source system 40 includes an X-ray controller 41, which triggers an X-ray source 42 producing pulsed beams of X-rays of high and low energy bands with dark (no X-rays) intervals between the pulses. X-ray source 42 includes a high voltage transformer 46 with a nominal primary voltage of 300 volts (peak) and having two secondaries of 75 kV each connected to an arrangement of high voltage diodes 47. These diodes are connected to an X-ray generating tube 43 such that during one set of alternate half cycles both transformer secondaries (150 kV) are connected across the X-ray tube. During the other set of half cycles, only one of the secondaries (75 kV) is placed across X-ray generating tube 43. All of the above source components are mounted within an oil tank and immersed in insulating oil.

X-ray controller board 41 receives AC voltage from the power distribution system and timing, control and interlock signals from the System Interface Board. Controller board 41 supplies energizing voltages to HV transformer 46, which is then adjusted based on the voltage developed across X-ray generating tube 43 monitored by a resistive voltage divider circuit 48. Controller board 41 also monitors the tube current during the low energy pulse of X-rays using resistive shunt 49 and uses the obtained value to adjust the tube filament voltage via filament transformer 50 to maintain the X-ray tube current at a constant value. The X-ray controller provides status and read-back signals to the host computer.

The inspection device also uses calibration shuttles placed next to the X-ray source to allow a programmable insertion of background or foreground materials into the beam during a calibration sequence. The purpose of the calibration shuttles is to check the stability of the device, since each sample of known materials should measure within certain specified limits, and to monitor the long term drifts. The shuttles contain an assortment of materials ranging from low-Z materials (plastics) to high-Z materials (metals) all made in strips of several different thicknesses.

The inspection device uses a filter drum that is a motor driven, spinning cylinder of lexan or other plastic and is lined with strips of brass aligned along its long axis. The strips are inserted into the X-ray beam to effect a filter for the high X-ray pulse (150 kVP) only. A timing wheel, consisting of a disk with slotted holes arrayed around the perimeter and mechanically coupled to the filter drum, acts in conjunction with an optical interrupter circuit to issue low beam and high beam timing pulses to the system interface board (SIB), and ultimately to the X-ray source and to the detector array electronics. One of the timing wheel holes is a double hole providing a synchronizing double pulse to the system interface board, thus providing the system with a positional reference to a specific set of filter drum strips for calibration of system timing to individual filter strips. This assembly is driven from a line-synchronous motor and thus all timing pulses and X-ray pulses are synchronized to line frequency providing a measure of line-frequency rejection of system errors.

FIG. 7 shows diagrammatically the hardware organization and the movement of data detected by transmission detector 60, scatter detectors 80 and 100, and dimension detector 120. The scatter and dimension detectors send the data over bidirectional communications links to a scatter interface board (SCIB) 150. Transmission detector 60 sends a sequence of voltages representing the responses of the individual detectors to the Analog to Digital bidirectional communications link. Both the SCIB 150 and the DIB 160 provide timing and sequencing signals to and from the attached detector arrays based on signals received from a System Interface Board (SIB) 180. The signals are distributed between the DIB and the SCIB by a System Interconnect Board 190.

A transputer board, the BO14 (195), receives data from DIB board 160, makes initial decisions as to whether the transmission data is attributable to "air" or scanned baggage. The transputer also performs air subtraction and then sends the processed data to "Skylink" interface card 199 which is plugged on to the first 1860 processing card 205.

The SCIB board contains a DSP processor (Motorola DSP 56166) which provides convenience and flexibility of programming and sequencing. The data rate into the SCIB is at a level that enables sufficient processing power. All SCIB memory is readable over the VME bus 192 in order to be able to perform memory and detector array diagnostics. The processor memory is "booted" from the host computer (80386) and does not require additional on board firmware. The distance, forward-scatter and back-scatter data sent to the SCIB are available in the SCIB data transfer RAM. The SCIB is read and written on the VME backplane via a fast VME bus interface by commercially available 1860 processor boards 205, 215 which act as VME bus masters.

The 1860 processor boards 1 (205) through 4 (215) communicate via the VME 192 and the VSB 210 busses in order to divide the computational work required among four processors. The decision rendered by the automatic software is communicated to the video card and the video display. The decision and bag image information can optionally be routed to computer networks which communicate to baggage control systems and image workstations.

System Interconnect Board 190 carries I/O signals to and from the detector arrays and distributes them to the DIB and the SCIB, as well as providing synchronizing signals from the SIB board to the DIB and SCIB boards. The System Interconnect Board also contains circuitry that provides the system serial number and system ID and reads the integrity of all cable interlocks including the cable interlocks of the scatter system cables and the detector system cables. This system ID and cables interlock shift register is connected to the SIB via the P2 VME connector and is read by the 80386 CPU.

In general, the recognition algorithm shown in FIG. 1A utilizes digitized transmission data 78, back-scatter data 98, forward-scatter data 118, and distance data 128. The raw data are calibrated using factory measured values and/or daily calibration values as well as pre-scan "air" and "dark" current values. The back-scatter data 98 is additionally normalized using distance data 128, and the forward-scatter data is additionally normalized using the transmission data 78, as will be described in detail later. Furthermore, the algorithm eliminates from further processing data attributable to "air" only; such data exhibits absorption values below a selected air threshold value.

Figure 8:
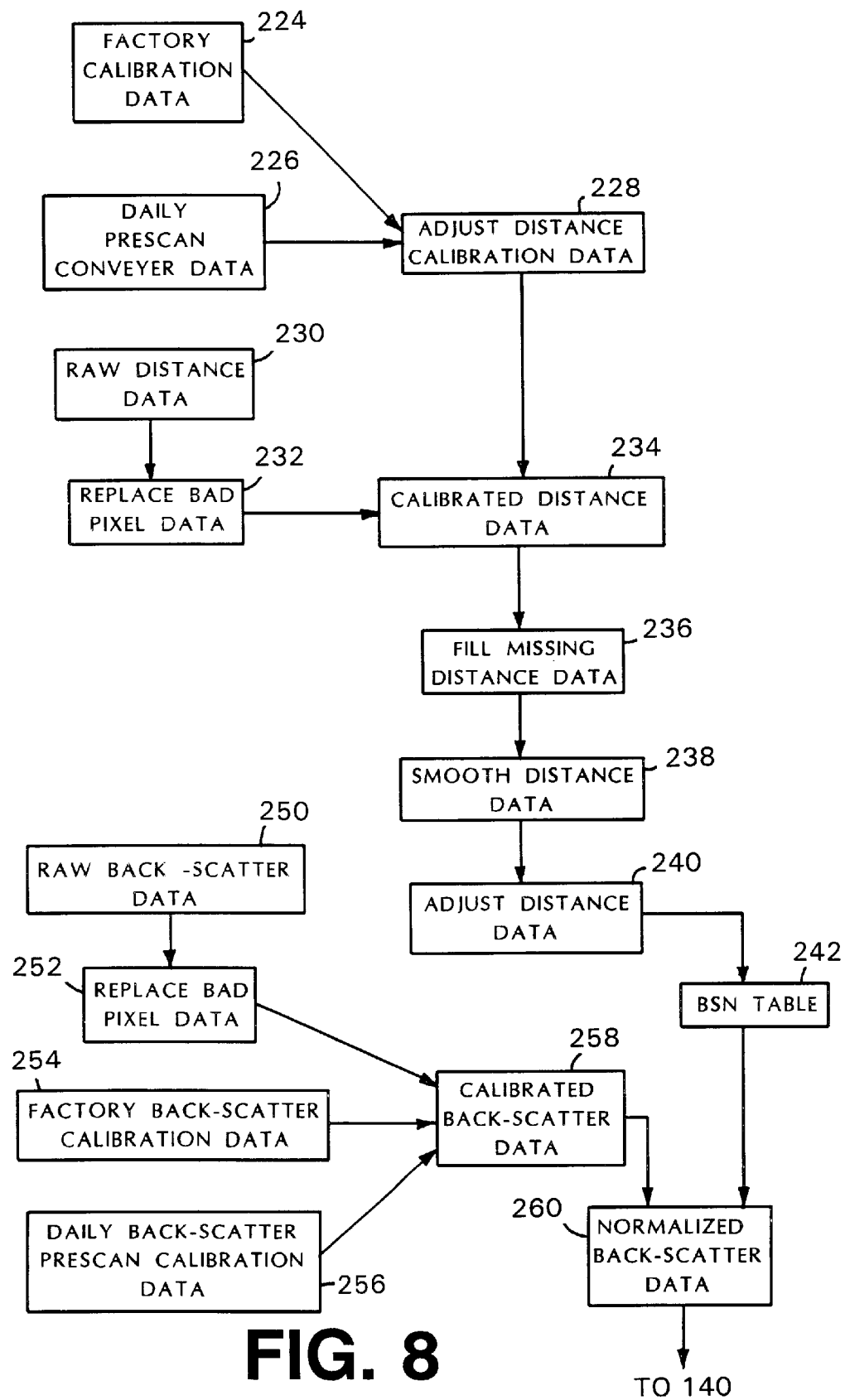
FIGS. 8 and 8A show diagrammatically calibration and normalization of the measured data.
Figure 8A:
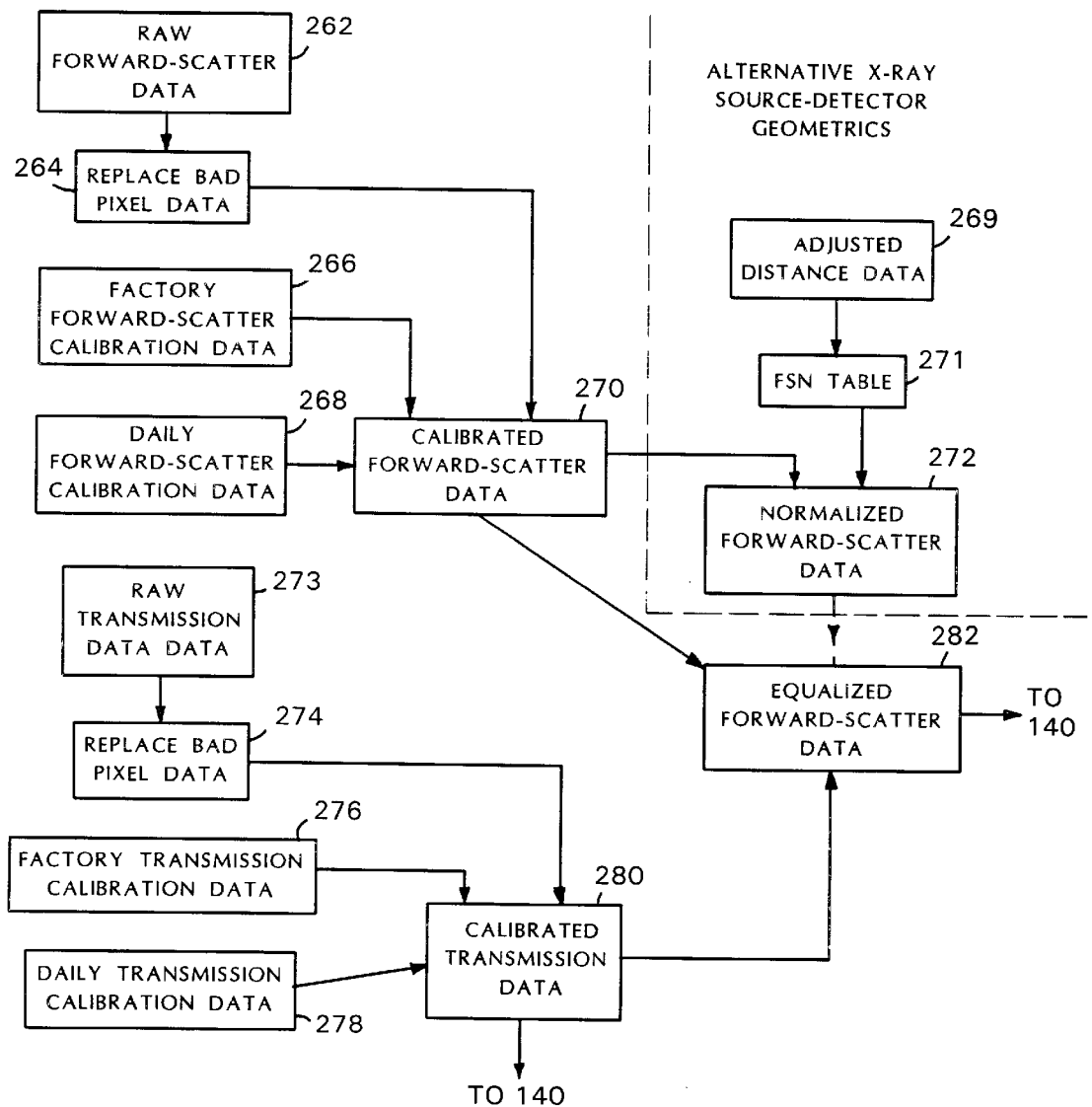

Specifically, as shown in FIGS. 8 and 8A, an I860 board and/or SCIB 150 performs calibration procedures for the acquired scatter and distance data. At preselected times, the system executes calibration sequences for X-ray detectors 60, 80 and 100, and dimension detector 120 against empty conveyor 20 to supplement factory calibration. This calibration is performed to account for potential drift due to external influences. Furthermore, the calibration sequences can detect failures of equipment where the detected calibration values substantially differ from the factory calibration values.

Dimension detector 120 executes at preselected times a calibration sequence against empty conveyor 20 to collect "daily prescan calibration data" (226) These data sets are used together with "factory calibration data" (224) in an "adjust calibration" procedure to obtain a set of "adjusted calibration data" (228). These calibration measurements are used to verify positioning values of distances and angles of IR LEDs 122 and PSDs 127. A set of "raw distance data" (230) is detected in a detection procedure with baggage 24B on moving conveyor 20. Then, the processor "cleans up" the acquired distance data (232) to replace bad pixels (which can be artifacts caused by rapidly changing IR reflectivity or by areas with very low reflectivity). The processor then calibrates the distance data using the "adjusted calibration data" (228), which set the maximum and minimum distance values, and computes the "adjusted distance data" (240). The processor may also use filling procedures (236) or smoothing procedures (238).

Back-scatter detector 80 also executes at preselected times a calibration sequence against empty conveyor 20 to collect "daily prescan calibration data" (256). After back-scatter detector 80 detects "raw back-scatter data" (250) with baggage 24B on moving conveyor 20, the processor replaces bad pixels (252) in the detected data set. "Daily prescan calibration data" (256) are used together with "factory calibration data" (254) in a calibration procedure that sets the scale and the offset in "calibrated back-scatter data" (258). The full scale is set in a way that the calibration data are at a fractional level, e.g., 15% level; however, other scales, including a non-uniform scale across the row of detected data, are possible. The processor then normalizes the calibrated back-scatter data (258) using a back-scatter normalization (BSN) look-up table (242). The BSN look-up table includes values that reflect the response of X-ray back-scatter detectors 86 including the geometry of collimator 84. One embodiment of the BSN look-up table includes values detected for a thin plexiglass plate mounted at varying heights from the conveyor belt (e.g. 0", 2", 4", . . . , 18") For each pixel, the BSN look-up table returns a value corresponding to the distance adjusted data (240); this value is multiplied by calibrated back-scatter data (258) to obtain "normalized back-scatter data" (260). Thus the normalized back-scatter data also accounts for varying detector efficiencies, due to solid angle variations with respect to the distance of the inspected surface to the individual back-scatter detectors, as well as electronic variations in gain and offset, and also compensates for the varying angle and field of view of the individual back scatter collimators.

Similarly, forward-scatter detector 60 collects "daily prescan calibration data" (268) detected with empty conveyor 20 and "raw forward-scatter data" (262).

The processor replaces bad pixels in the "forward-scatter data" (262) and also calibrates data using "factory calibration data" (266) and the "daily prescan calibration data" (268). The "daily prescan calibration data" define the full scale and the data detected with no X-rays define the zero. The full scale is set in a way that the calibration data are at a fractional level, e.g., 50% level; however, other scales, including a non-uniform scale across the row of detected data, are possible. Furthermore, the processor may also execute a "bad pixel removal" algorithm on both back-scatter and forward scatter data. This algorithm removes different noise data such as data caused by cosmic rays.

The re-scaled "calibrated forward-scatter data" (270) are then equalized by using transmission array data to account for differences in absorption of various objects and contents within baggage 24B. Since, in the X-ray source-detector arrangement of FIG. 1, the distance to the front-scatter surface is defined by the position of conveyor 20 and is fixed, no height normalization of "calibrated forward-scatter data" (270) is needed. However, for other arrangements (e.g., the source-detector arrangement disclosed in the U.S. Pat. No. 5,319,547) "calibrated forward-scatter data" (270) may need to be normalized. This normalization uses a forward-scatter normalization (FSN) table (271) and "adjusted distance data" (269) comprising measured local distances between the front-scatter surface of the examined baggage and forward-scatter detector array 106.

The "calibrated forward-scatter data" (270) depend strongly on the X-ray flux's reaching the front scatter surface, and this X-ray flux, in turn, depends on the objects within baggage 24B. Therefore, the "calibrated forward-scatter data" (270) (or normalized forward-scatter data" (272)) is equalized by "calibrated transmission data" (280) detected by transmission detectors 68. This equalization takes the form:

$$Hfront = (((RawHfront/NormHfrontair) * (exp(beta*Htrans) - 1) * factoryHfrontScale)$$

where

Hfront is the equalized front scatter data for High energy pulse;

RawHfront is the raw front scatter data (unequalized);

NormHfrontair is the prescan measured air data;

beta is a constant equal to $0.0028 = (\log_{10} 819)$;

Htrans is the transmission data for the High energy pulse;

Factory HfrontScale is equal to (factory Hfrontair/FactoryHfrontCal), where FactoryHfrontCal is the measured response to a ¼" plexiglass sheet.

The low energy data is similarly equalized using the low energy data and measurements. The "equalized forward-scatter data" (282) is quite independent of the contents and size of baggage 24B. The "normalized back-scatter data" (260), the "equalized forward-scatter data" (284), and "calibrated transmission data" (280) are used in the recognition algorithm that recognizes a specific material of interest. The recognition algorithm includes several high level algorithms described first generally and then in detail.

The objectization algorithm (140) groups pixels into aggregates called regions that are further processed into objects. The processing starts with regionization, which attempts to partition the pixel data into regions of similar data values. This reduces the number of data elements, which must be separately handled at later states of the algorithm, by a factor of 10 to 100. Regions that meet certain threshold criteria, such as size and material composition, are further processed into objects, which represent configurations of material of similar composition, and which probably represent real items, or components of items, in the inspected luggage.

The transmission data are spatially correlated with both the back-scatter data, and forward-scatter data to permit comparisons and calculations between different types of data corresponding to the same region of the examined item. This objectization algorithm uses many heuristic clues from all of the scanned images such as edges, shapes, material analysis, and others, to accurately recognize and define individual regions and objects in the examined baggage.

Then the recognition routines are employed. These objects are evaluated by several algorithms, called modules, which accurately measure (much more accurately than the region information) various physical parameters such as the material composition (142), total object mass (132a), estimated mass density (132b), front or back scatter return values, and particular object configurations and heuristics, such as thin, sheetlike objects hidden in linings and under surfaces (133). Each module has a number of parameters (131) that govern its operation and execution. These parameters, selectable on site with supervisor level access, offer a range of mass and sensitivity settings for several different threat types (e.g., explosives, drugs, money, etc.). These parameters effectively adjust the false alarm vs. detection trade-offs and allow the machine to be configured in the field to meet a wide variety of operational and detection requirements.

These algorithm modules send the measured and derived object values to a threat decision module (135) which makes decisions on an object-by-object basis according to the decision parameter setting 131. The threat decision module can signal to a baggage control system to reject automatically or re-route the items that have at least one threat object.

Also referring to FIG. 10, conveyor 20 automatically sorts the examined items of baggage using a pusher 290. The items of baggage that have no threat object are cleared to the final destination 292. The "suspect" items of baggage are sent for further inspection to a CT scanner 294 or another inspection device. An attached workstation 296, including an operator interface, allows an operator 298 to manipulate and view images of the rejected items or luggage and, based on his decision, to clear rejected items or to send them on to another inspection area for hand search or further inspection using the computed tomography.

Since the inspection device uses polychromatic radiation, the algorithm must account for the energy shift as it is filtered by materials in the item under inspection, i.e., beam hardening. As described in prior art (e.g., Lehmann et al., "Generalized Image Combinations in Dual KVP Digital Radiography," *Medical Physics*, Vol. 8, p.659, 1981, and references cited therein) absorption of any material can be expressed as a linear combination of two basis materials. This transformation serves to convert the measured X-ray intensities at the two energies to an equivalent representation in thickness of the two basis materials. The measured X-ray intensities are non-linear, with increasing thickness of materials due to the effect of X-ray beam hardening; however, the basis materials representation is completely linear with increasing attenuation and provides a measurement of material properties that is independent of overlying materials and densities. The present algorithm uses iron, a high atomic number material, and boron, a low atomic number material, as basis materials. Boron (B) and iron (I) were selected because their atomic numbers bracket the range of atomic numbers of the most common objects expected in baggage. (To assure accurate decomposition at low energies, a concept of "pseudo-iron" instead of iron is used.) In the boron and "pseudo-iron" (denoted as iron hereinafter) basis set, absorption data of iron has transformation (B=0, I) and absorption data of pure boron has transformation (B, I=0). Detected intensities at high and low energies ($I_h$, $I_l$) are transformed to generate a set of (H,L) values as follows:

$$H = \log_{10}(I_{ho}/I_h)*819$$

$$L = \log_{10}(I_{lo}/I_l)*819$$

wherein $I_h$ and $I_l$ are detected X-ray intensities at the high and low energies, respectively, $I_{ho}$ and $I_{lo}$ are detected X-ray intensities at the high and low energies, respectively, unattenuated by the examined baggage (i.e., no baggage in the fan beam), and 819 is a scaling constant. Then the transformation from (H, L) to (B, I) is performed by reading B and I values from the CBI lookup table described in detail in Appendix I.

The inspection device takes data for all pixels, and the computer system calculates the (H, L) data. the (B, I) data is then looked up using the BI table and the information is added to the pixel data record. The computer may also perform 1 or 2 dimensional filtering, averaging, or other processing of the pixel (H, L, B, I) data to reduce the number of processed pixels.

A "regionization" procedure groups together small groups of like pixels and calculates their aggregate attributes. The "regionization" procedure basically averages data over many pixels; this is needed due to the high noise in the image. However, if data is averaged over dissimilar pixels or over pixels belonging to different objects, then the averaging process will be highly detrimental. First, a set of seed points are generated from which the regions will grow. The seed points can be selected using different methods, for example, laying down a pre-determined 3×3 pixel grid, or placing seeds only on areas where the gradient of the attenuation values is low, such as on a "flat." Then the average values of (H, L) are calculated over a 3×3 box for each seed point.

The regions are then allowed to grow by examining neighboring pixels to see if they are within certain ranges of these seed values, e.g., two times the expected noise (due to photon counting statistics) at both high and low energy attenuations. Additional conditions may also be applied. If they are, they are added to the growing region and their values accumulated into the region values. At a certain size, e.g., 10 or 50 lines, the region is stopped from growing and is then considered mature. Each region is characterized as being either a flat region or a ramp region using a gradient computation such as the Sobel. Any pixels which do not meet grow region criteria are left unregionized.

A "P-space mapping" procedure maps the (B, I) data to a P-space which represents different types of material but is independent of the thickness of each material (i.e., the P value is constant for different thicknesses):

$$P = \left(I - B\frac{\alpha_{MAT}}{(1-\alpha_{MAT})}\right) * 5000$$

wherein $$\alpha_{MAT} = \frac{I_{MAT}}{B_{MAT} + I_{MAT}}$$

is a target material property that is independent of thickness and 5000 is a scaling constant. For each region, P values are added to the (H, L, B, I) data in the region data record.

An "Accept Points" procedure detects accept points that are in a flat region and have neighboring regions of significantly lower B value. This way a threat substance is detected at the edge of an object or in a region of changing thickness. The accept points are then scored in a substance detection procedure.

A composition analysis scoring procedure scores a selected region by reference to other nearby regions. Scoring starts from a region containing an accept point and this region is compared with neighboring regions. The region itself and the region which is being scored against must satisfy a number of selected criteria, such as minimum sizes and attenuations, before scoring is performed. In comparing two regions, the score is given by a constant minus ΔP, wherein $\Delta P = P_T - P_B$ (i.e., the change in P values from one region to the other). The score equals 100−ΔP. The scoring works outward in ranks from the center of the region of interest. Once one acceptable region with a positive score is found, scoring then continues only to the end of the current rank. The best scoring region at the current rank is the score of the region.

A "quick grow" procedure converts multiple regions into a larger region which would be a proto-object. Since the above-described scoring takes place at the edges of an object (or in regions of an object where the thickness is changing), an evolution procedure is needed to fill in the object and to accumulate higher statistics than those available within a single region. The "quick grow" procedure starts from regions which have achieved a minimum score and grows to nearby regions which satisfy the following criteria:

(1) A region must be uphill from the sponsoring region; or
(2) If a region is downhill, it must not be lower in B than the B of the background against which the seed region scored;
(3) If it is downhill, it must differ in B from the sponsoring region by less than 10% of the B of the sponsoring region;
(4) The difference in B between it and the sponsoring region must not exceed a threshold, e.g., 0.6;
(5) The difference in filtered P between a region and the sponsoring region must not exceed a threshold, e.g., 400.

The new regions of growth must not be more than a fixed distance, e.g., 40 lines, from the original region.

A "threat potential" procedure evaluates the "threat potential" function over an entire grow region. This function yields a score and a bias value based on the size of the gradient in P divided by the gradient in H. If the grow region corresponds to a true threat substance, the scores will be high and the bias low. If the grow region corresponds to a substance with an alpha value which is not the alpha value under consideration then the score should be lower and the bias would be higher. "Threat potential" also provides a heuristic measure of the object's physical density. Denser objects tend to produce higher "threat potential" scores, all other parameters being equal. This way the "threat potential" procedure evaluates grow regions to either qualify them or to disqualify them from further processing.

Those regions that survive the "threat potential" procedure are processed for object "knitting." This module looks for grow regions that may be part of the same object but are overlaid with another object (such as a clothes hanger) which divides the object into two separate grow regions. These grow regions are "knitted" together if they meet certain criteria with respect to one another. The objective of the "knitting" procedure is to result in complete objects, despite other overlapping materials and objects, so as to be able to apply the "threat object" detection algorithms and thresholds.

The "threat object" detection algorithms apply the algorithm parameter settings to various measured characteristics of each identified object to arrive at a threat object decision. Criteria such as object mass, estimated density, composition analysis ($Z_{eff}$), texture, shape and background, and configuration characteristics, such as clutter and placement (which could be evidence of a detonator or electronics), are evaluated to arrive at a decision for each object.

The algorithm can recognize an object made of a specific material of interest located in the examined item utilizing X-rays transmitted through or scattered from the target object and X-rays transmitted near but not through the target object to effectively remove the effects of underlying or overlying materials. This recognition can start by identifying an edge of the target object and then progressively examining adjacent pixels.

A "blasting cap" or detonator detector algorithm examines the image for elements having nearly cylindrical shapes which would represent the shell of a blasting cap or an internal delay element. Further discrimination is made based on the dimensions of the cylinder, absolute attenuation values, the attenuation relative to background, and the H/L ratio. An additional detection mode exists which looks solely for small volumes of heavy metals, such as lead azide or lead styphnate, which are often found in blasting caps. Such volumes are characterized by large local gradients in H and L with a relatively large H/L ratio.

The thin sheet explosive detection algorithms target various configurations of sheet explosive (or alternatively for other contraband by setting appropriate parameters 131) in baggage. The individual modules search for various configurations including the following configurations:

(a) sheet explosive in a pocket of the baggage;
(b) sheet explosive lining side of the baggage;
(c) sheet explosive in middle of the baggage; or
(d) sheet explosive seen on edge.

Each of these configurations is detected by specific signatures in various combinations of the forward-scatter data of the high (H) and low (L) energies, the back-scatter H and L data, the transmission H and L data, and the dimension data. These combinations include data resulting from a processing sequence on the basis data, as follows:

(a) the gradient of the forward-scatter L and back-scatter L squared; this signature emphasizes thin, dense materials on the surfaces;
(b) transmission "sheet edge" magnitude and direction which is calculated for small gradient edge in the transmission data (H, L, or H+L), deriving a line of pixels normal to the selected edge and "P" averaging the pixels on the lower valued and upper valued sides of the selected edge separately, then performing the ΔP calculation, and marking all edge pixels that have a sufficiently small difference;

(c) estimated forward-scatter data and back-scatter data based on the H and L attenuations of the transmission data (allowing materials analysis) and assuming uniform distribution; or (d) scatter ratio of H/L for both forward-scatter data and back-scatter data; this is a signature of an X-ray material property equivalent to effective atomic number ($Z_{eff}$) for the object that is causing the scattered X-rays.

The data sets of the above-described processing sequences are combined to create new properties of the inspected luggage as follows:

1. anomalous scatter relative to other side of baggage;
2. anomalous scatter relative to estimated scatter return;
3. "transmission sheet" pixels spatially correlated with high "sheet scatter" signals from at least one side of the examined baggage;
4. "transmission sheet" pixels with coordinated edges (straight lines); and
5. high scatter return with the scatter ratio within a given range.

If an object meets or exceeds the set decision parameters, then the object is identified on the image sent to the attached workstation with a red color overlay for bulk and green for sheet superimposed on the indicated object in the gray-scale X-ray image. Additionally, a message or signal is sent to a conveyor control system in order to properly direct the item of luggage to the appropriate destination for further inspection.

Figure 9:
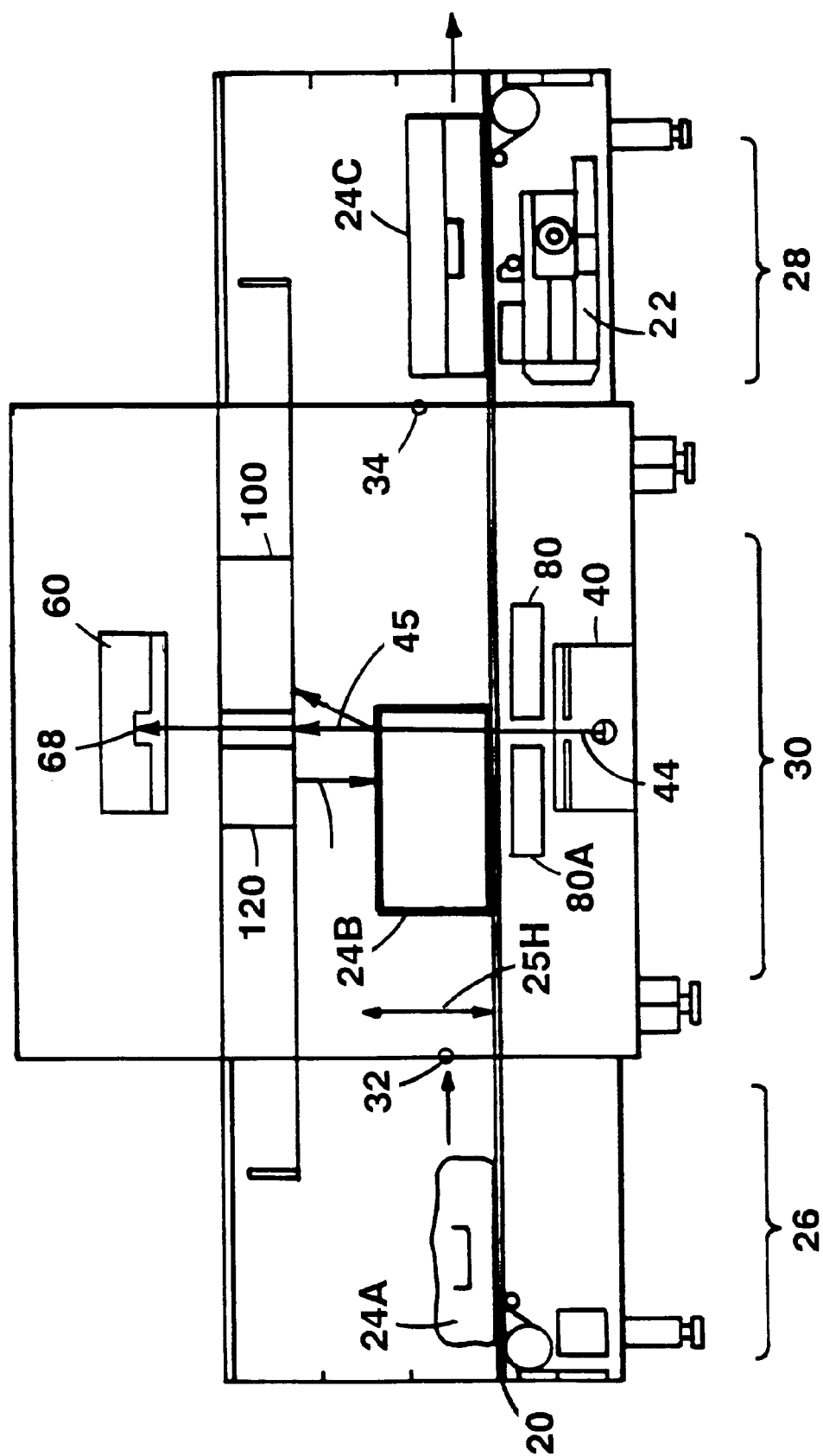
FIG. 9 shows schematically another X-ray source detector geometry of the X-ray baggage inspection device of FIG. 1.

Alternative Embodiments:

Another embodiment of the invention uses an alternative X-ray source-detector geometry shown in FIG. 9. The X-ray source system 40, located below conveyor 20, emits fan beam 45 directed through examined baggage 24B toward X-ray transmission detection system 60. X-ray radiation scattered from the bottom layers of baggage 24B is detected by back-scatter detection systems 80 and 80A. X-ray radiation scattered from the top layers of baggage 24B is detected by forward-scatter detection system 100.

Figure 5C:
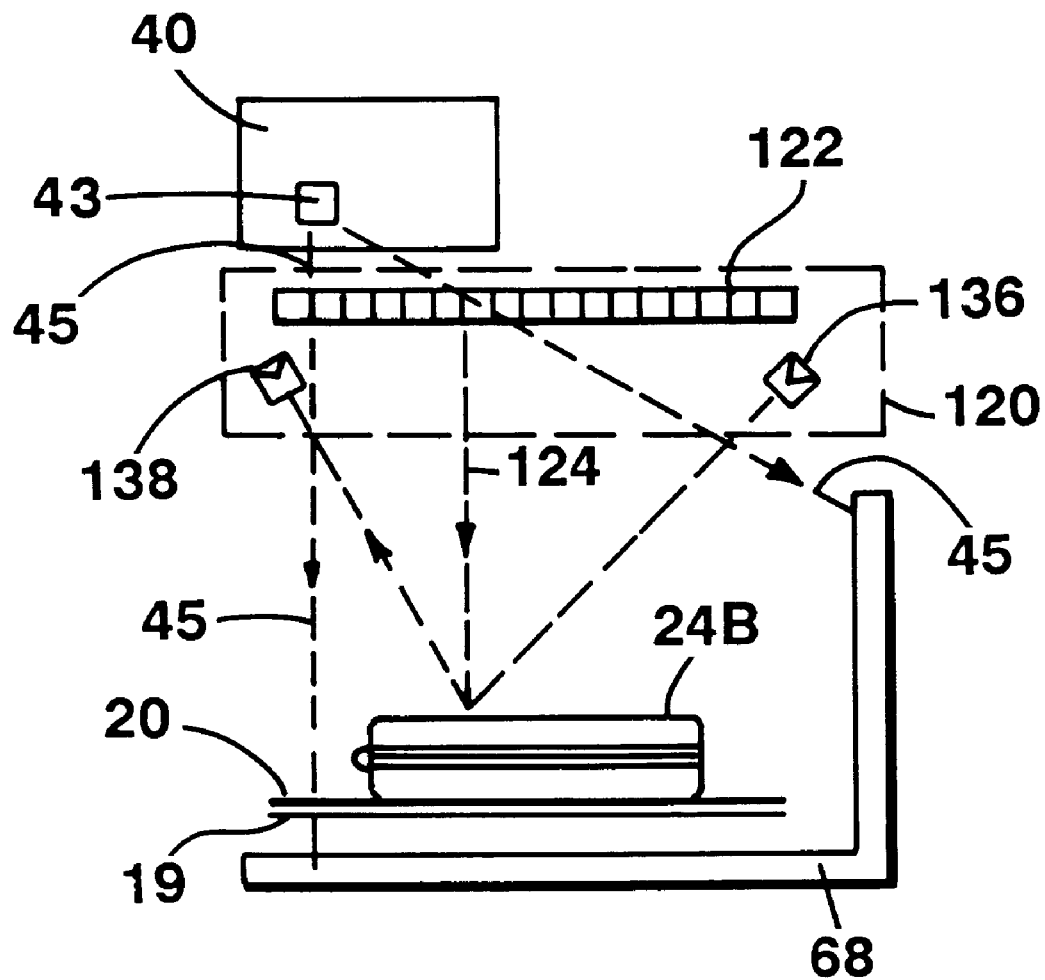
FIG. 5C shows schematically an alternative embodiment of the dimension detector.

Dimension detector 120 has several alternative embodiments. For example, referring to FIG. 5C, another type of optical dimension detector 120 includes an array of strobed 40 IR laser diodes 122 sequentially emitting infrared beams 124, which irradiates the top surface of conveyer 20 or baggage 24B. The reflected IR light is detected by two CCD cameras 136 and 138 mounted on each side of the IR array. The distance data is calculated by triangulation by a processor based on the geometry of the illuminating IR diode and the signals received from CCD cameras 136 and 138. As baggage 24B moves on conveyor 20, dimension detector 120 collects for each pixel the distance data corresponding to the surface scanned by the CCD camera.

Alternatively, dimension detector 120 is an optical detector that includes one or two "light curtains" positioned across the entrance to 30 inspection region. Each light curtain includes a set of laser diodes (or LEDs or other collimated light sources), positioned on one side of the inspection region, and the corresponding set of light detectors (e.g., diodes) positioned on the opposite side of the inspection region. As baggage 24B is transported on conveyor 20, the light of the light curtain at locations corresponding to the dimensions the baggage is blocked. Based on these locations, the optical detector determines the size of baggage 24B.

Alternatively, dimension detector 120 includes an ultrasonic detector such as ultrasonic systems available from Migatron Corp., 935 Dieckman Rd., Woodstock, Ill. 60098. The ultrasonic detector includes one or more ultrasonic transmitters (i.e., piezoelectric crystals resonating at a desired frequency) that emit ultrasound waves directed toward moving baggage 24B. An ultrasonic receiver, which can be the same piezoelectric crystal operating alternatively as a transducer and receiver, detects waves reflected from the surface of baggage 24B. A processor determines the distance data based on the frequency shift between emitted and detected waves. The discrete distance data from the detector to moving baggage 24B is measured by a commercially available proximity sensor RPS-100/200/300/325 coupled to an RPS-500 analog ranging card (made by Migatron). To scan over the surface of the measured baggage, the ultrasonic detector may include a few transducers that are linearly displaced or may include an array of transducers. Alternatively, the ultrasonic detector may include an array of phased transducers, operating as emitters and detectors, which scan over the surface of the measured baggage.

Alternatively, dimension detector 120 is a mechanical sensor that includes a set of "fingers" displaced or bent by the moving baggage. The detector computes the distance data based on the displacement or bending angle of the fingers.

Alternatively, back-scatter detector 80 or front-scatter detector 60 may be any one of several alternative detector types, such as a system that measures each individual X-ray photon and its energy by use of a pulse height analyzer and an energy-proportional scintillator.

Alternatively, the back-scatter detector array 80, including NaI crystals 37, may be replaced by one or a small number of long scintillators monitoring the same area as in the embodied array. Position sensing is accomplished by having two or more PMTs viewing the cintillator(s). Individual scintillation events are processed and the position of the scintillation reconstructed based on the relative strength of the various PMT signals.

Alternatively, the front-scatter detector or array 100 including $CdWO_4$ crystals 106 may be replaced by one r a small number of long scintillators monitoring the same area as in the embodied array. Position sensing is accomplished by having two or more PMT's viewing the scintillator(s). Individual scintillation events are processed and the position of the scintillation reconstructed based on the relative strength of the various PMT signals.

Alternatively, the sample and hold circuit 93 may be replaced by a pulse height analyzer and other associated circuitry for processing individual X-ray scintillations from crystals 87. The spectral response may aid in the detection process in that detected low energy scatter X-rays are more likely to originate near the top of the inspected item. Also, heavy metal (High Z) materials within the item produce characteristic fluorescent which under suitable circumstances will appear as a spectral peak.

Alternatively, the sample and hold circuit for front scatter may be replaced by a pulse height analyzer and other associated circuitry for processing individual X-ray scintillations from crystals 106. The spectral response may aid in the detection process in that spectral peaks may be observed that are characteristic of specific explosives or other contraband material. Also, heavy metal (High Z) materials within the item produce characteristic fluorescent which under suitable circumstances will appear as a spectral peak.

Alternatively, the back-scatter detector array 86 may have filtration material placed in front of some or all detectors to emphasize selected spectral components of this received scatter radiation.

Alternatively, the front-scatter detector array 106 may have filtration material placed in front of some or all detectors to emphasize selected spectral components of this received scatter radiation.

Alternatively, filtration material may be placed in front of X-ray source system 40 or in selected positions on the rotating filter drum within the X-ray source system.

Alternatively, multiple back-scatter detector arrays 80 may be used at differing distances from the beam plane and/or with differing filtration material in front of the detectors.

Alternatively, multiple front-scatter detector arrays 100 may be used at differing distances from the beam plane and/or with differing filtration material in front of the detectors.

Appendix I

Absorption data of any other material now expressed in (H, L) terms is rapidly transformed using a BI look-up table expressing the corresponding thicknesses of boron and iron (I, B). The BI look-up table was generated to account for important physical processes in the generation, absorption, scattering and detection of X-ray radiation. The generated primary spectrum of X-rays reflects the production of bremsstrahlung and characteristic radiation in the anode modified by the absorption of the glass tube and filtering within the tube (Lohmann model 160I25HA). An adequate model of bremsstrahlung and characteristic radiation emitted from the tungsten anode is given by H. E. Johns and J. R. Cunningham in *The Physics of Radiology*, C. C. Thomas, 4th ed., 1983. The radiation model also includes emitted K-alpha and K-beta fluorescence. As described above, the source system emits pulses of radiation at 75 kVp and 150 kVp voltage potentials. When the device operates at 60 Hz, each pulse has duration of about 8 msec with rise and fall times of about 0.5 msec and some overshooting. The transient and overshoot effects broaden the X-ray spectrum to a minor degree. This effect was modeled empirically using a bimodal kvp model for treating non-constant anode voltages. The bimodal kvp model was applied separately to the high and low beam.

The absorption process hardens the X-ray spectrum by selectively removing lower energy photons from the beam, i.e., filtration of low energies. The X-ray tube has an inherent filtration due to absorption in the glass of the tube, beryllium window and the tungsten anode itself. The primary beam spectrum emerging from the tube is described in Fewell et al. (Fewell, T. R., R. E. Shuping and K. R. Hawkins, Jr., 1981; *Handbook of computed tomography X-ray spectra*, Bureau of Radiological Health, HHS publication FDA 81-8162, pp. 101). There is some additional filtration due to the arrangement of the inspection device that is also taken into account. The filtration due to air is a relatively insignificant factor that is ignored.

The model also accounts for the output response of the detector and the associated electronics. Any electronic offset is removed by subtraction of the dark current signal sampled between pulses and accumulated for an identical duration. (Alternatively, depending on the X-ray detector, the dark current signal can be accumulated before the examined baggage is scanned.) Thus, the linear attenuation with dark current subtracted is a measure of the X-ray flux incident on the detector. The detector efficiency was taken into account.

When $CdWO_4$ scintillating crystals are used, the detection efficiency is almost 100%. When $GdOS_2$ scintillating paper is used, the detection efficiency is much lower especially for higher energy X-rays. Monte Carlo simulations are used to model the detector efficiency for different angles of incidence, different scintillator thicknesses and types at different X-ray energies.

The actual detector output response $R_D(E)$ depends on the amount of energy absorbed, on the conversion efficiency to visible light, and the efficiency of the optical detector. Detection output due to photons of energy, E, with a target thickness, t, is then:

$$O(E,t)=kI(E)\exp(-t_F\mu_F(E)/\rho_F)\exp(-t_T\mu_T(E)/\rho_T)R_D(E)$$

wherein
k=proportionality constant;
O(E,t)=detector output;
I(E)=beam strength before filtration;
$t_F, t_T$=thickness (gm/cm$^2$) for filter and target material;
$\mu_F/\rho_F$=mass attenuation coefficient for filtration (including inherent);
$\mu_T/\rho_T$=mass attenuation coefficient for target;
$R_D(E)$=detector electronic output response for an incident photon of energy E.

Integrating over all energies in the beam (0 to E-max), the output for a polychromatic spectrum of X-ray photons is given by:

$$O(t) = \int_0^{E\text{-max}} O(E, t)\, dE.$$

The logarithmic attenuation, M, due to the target material is then $$M = -ln[O(t)/O(0)].$$

For a dual energy X-ray beam, the logarithmic attenuation for the high and low energy beams, H (or $M_H$) and L (or $M_L$), will differ due to the differences in their beam strength spectra I(E) and the differing filtration employed for the two beams. The attenuations H and L were computed using the above mathematical beam model and suitable numerical approximations and numerical integration techniques. The computed attenuations were benchmarked against measurements taken on Al and plexiglas calibration stepped wedges.

There are several numerical artifacts that distort somewhat the H and L values from their "true" values, i.e., values unaffected by counting statistics, electronic noise and finite dynamic range. Some of these effects are (1) non-linearity in the linear-to-log mapping, (2) clipping, (3) air subtraction, (4) electronic noise, (5) offset in linear-to-log conversion, and (6) digitization effects. The BI table reflects these effects. A conversion table was generated to translate the "true" attenuations into those expected by averaging many measured replicates.

The BI table was generated in a three step process. In the first step, H and L attenuation values for a parameterized net of boron and iron thicknesses were computed. For computing filtration thicknesses and detection efficiencies, the beam was assumed to be directed incident to the detectors at a 10° angle and hypothetical targets consisted of 16 possible boron thicknesses and 19 overlaying iron thicknesses. The calculation produced a total of 304 (H,L) attenuations which fully explore the relevant BI space.

In the second step, the 304 (H,L) attenuations (provided in Table I) at known BI thicknesses are used to interpolate BI thicknesses that would occur at each point on an (H,L) grid. The grid was defined by spacing H and L at two K-unit intervals in the 0 to 400 K-unit range, at four K-unit intervals in the 404 to 1000 K-unit range and at eight K-unit intervals in the 1008 to 3000 K-unit range. The (H, L) grid point was then output to a file along with the interpolated estimate for the associated B and I value. Only grid points lying within the physical range of interest were utilized.

In the third step, the output file of H-L-B-I data was reordered sequentially, first by ascending H value and secondarily by ascending L value. This file is then rewritten as a more compact binary file (CBI file). The latter file may be corrected for small empirical shifts in alpha, observed for targeted detection material behind significant absorber thicknesses. At the same time, the file is extended to contain (H, L) grid points with negative values for boron. This was necessary since, for example, an iron absorber (B=O), subject to random measurement errors in H and L, tends to produce positive and negative B data values with equal likelihood. Also, materials such as copper with Z larger than Z of iron require negative boron values to be adequately represented.

TABLE I

| I | Boron | Iron | HI | LO |
|---|---|---|---|---|
| 1 | .000 | .000 | .00 | .00 |
| 2 | .200 | .000 | 10.43 | 13.05 |
| 3 | .400 | .000 | 20.61 | 25.76 |
| 4 | .800 | .000 | 40.59 | 50.63 |
| 5 | 1.200 | .000 | 60.35 | 75.18 |
| 6 | 1.800 | .000 | 89.84 | 111.72 |
| 7 | 2.400 | .000 | 119.26 | 148.10 |
| 8 | 3.200 | .000 | 158.44 | 196.50 |
| 9 | 4.400 | .000 | 217.24 | 268.95 |
| 10 | 6.000 | .000 | 295.67 | 365.27 |
| 11 | 8.000 | .000 | 393.76 | 485.23 |
| 12 | 11.200 | .000 | 550.71 | 676.21 |
| 13 | 16.000 | .000 | 786.09 | 960.73 |
| 14 | 23.200 | .000 | 1139.07 | 1385.68 |
| 15 | 32.000 | .000 | 1587.01 | 1950.21 |
| 16 | 60.000 | .000 | 2973.75 | 3149.24 |
| 1 | .000 | .010 | 1.87 | 13.81 |
| 2 | .200 | .010 | 12.20 | 26.89 |
| 3 | .400 | .010 | 22.44 | 39.26 |
| 4 | .800 | .010 | 42.50 | 63.77 |
| 5 | 1.200 | .010 | 62.32 | 88.15 |
| 6 | 1.800 | .010 | 91.86 | 124.56 |
| 7 | 2.400 | .010 | 121.31 | 160.85 |
| 8 | 3.200 | .010 | 160.53 | 209.13 |
| 9 | 4.400 | .010 | 219.36 | 281.37 |
| 10 | 6.000 | .010 | 297.82 | 377.39 |
| 11 | 8.000 | .010 | 395.92 | 496.95 |
| 12 | 11.200 | .010 | 552.87 | 687.29 |
| 13 | 16.000 | .010 | 788.25 | 970.94 |
| 14 | 23.200 | .010 | 1142.10 | 1394.87 |
| 15 | 32.000 | .010 | 1589.26 | 1960.48 |
| 16 | 60.000 | .010 | 2974.08 | 3149.55 |
| 1 | .000 | .020 | 3.72 | 26.99 |
| 2 | .200 | .020 | 13.88 | 40.21 |
| 3 | .400 | .020 | 24.08 | 52.61 |
| 4 | .800 | .020 | 44.19 | 76.97 |
| 5 | 1.200 | .020 | 64.06 | 101.18 |
| 6 | 1.800 | .020 | 93.68 | 137.38 |
| 7 | 2.400 | .020 | 123.18 | 173.52 |
| 8 | 3.200 | .020 | 162.46 | 221.61 |
| 9 | 4.400 | .020 | 221.34 | 293.58 |
| 10 | 6.000 | .020 | 299.85 | 389.26 |
| 11 | 8.000 | .020 | 397.98 | 508.40 |
| 12 | 11.200 | .020 | 554.96 | 698.10 |
| 13 | 16.000 | .020 | 790.35 | 980.92 |
| 14 | 23.200 | .020 | 1144.19 | 1403.86 |
| 15 | 32.000 | .020 | 1591.48 | 1971.16 |
| 16 | 60.000 | .020 | 2974.40 | 3149.85 |
| 1 | .000 | .040 | 7.37 | 51.66 |

TABLE I-continued

| I | Boron | Iron | HI | LO |
|---|---|---|---|---|
| 2 | .200 | .040 | 17.32 | 64.82 |
| 3 | .400 | .040 | 27.37 | 77.33 |
| 4 | .800 | .040 | 47.41 | 101.74 |
| 5 | 1.200 | .040 | 67.32 | 125.86 |
| 6 | 1.800 | .040 | 97.05 | 161.87 |
| 7 | 2.400 | .040 | 126.64 | 197.78 |
| 8 | 3.200 | .040 | 166.03 | 245.55 |
| 9 | 4.400 | .040 | 225.04 | 317.04 |
| 10 | 6.000 | .040 | 303.66 | 412.06 |
| 11 | 8.000 | .040 | 401.89 | 530.42 |
| 12 | 11.200 | .040 | 558.96 | 718.95 |
| 13 | 16.000 | .040 | 794.39 | 1000.18 |
| 14 | 23.200 | .040 | 1148.24 | 1421.43 |
| 15 | 32.000 | .040 | 1595.82 | 1993.43 |
| 16 | 60.000 | .040 | 2975.04 | 3150.44 |
| 1 | .000 | .060 | 10.98 | 74.46 |
| 2 | .200 | .060 | 20.79 | 87.43 |
| 3 | .400 | .060 | 30.72 | 99.97 |
| 4 | .800 | .060 | 50.63 | 124.46 |
| 5 | 1.200 | .060 | 70.52 | 148.62 |
| 6 | 1.800 | .060 | 100.27 | 184.59 |
| 7 | 2.400 | .060 | 129.92 | 220.40 |
| 8 | 3.200 | .060 | 169.39 | 267.97 |
| 9 | 4.400 | .060 | 228.51 | 339.10 |
| 10 | 6.000 | .060 | 307.25 | 433.59 |
| 11 | 8.000 | .060 | 405.59 | 551.28 |
| 12 | 11.200 | .060 | 562.76 | 738.76 |
| 13 | 16.000 | .060 | 798.26 | 1018.61 |
| 14 | 23.200 | .060 | 1152.17 | 1438.34 |
| 15 | 32.000 | .060 | 1600.05 | 2014.97 |
| 16 | 60.000 | .060 | 2975.68 | 3151.01 |
| 1 | .000 | .090 | 16.33 | 105.82 |
| 2 | .200 | .090 | 26.00 | 118.50 |
| 3 | .400 | .090 | 35.80 | 130.98 |
| 4 | .800 | .090 | 55.52 | 155.54 |
| 5 | 1.200 | .090 | 75.32 | 179.78 |
| 6 | 1.800 | .090 | 105.04 | 215.80 |
| 7 | 2.400 | .090 | 134.71 | 251.55 |
| 8 | 3.200 | .090 | 174.25 | 298.97 |
| 9 | 4.400 | .090 | 233.49 | 369.74 |
| 10 | 6.000 | .090 | 312.38 | 463.65 |
| 11 | 8.000 | .090 | 410.86 | 580.53 |
| 12 | 11.200 | .090 | 568.20 | 766.73 |
| 13 | 16.000 | .090 | 803.84 | 1044.81 |
| 14 | 23.200 | .090 | 1157.85 | 1462.55 |
| 15 | 32.000 | .090 | 1606.22 | 2046.03 |
| 16 | 60.000 | .090 | 2976.61 | 3151.69 |
| 1 | .000 | .120 | 21.60 | 134.49 |
| 2 | .200 | .120 | 31.19 | 146.94 |
| 3 | .400 | .120 | 40.89 | 159.34 |
| 4 | .800 | .120 | 60.47 | 183.89 |
| 5 | 1.200 | .120 | 80.17 | 208.17 |
| 6 | 1.800 | .120 | 109.81 | 244.23 |
| 7 | 2.400 | .120 | 139.47 | 279.99 |
| 8 | 3.200 | .120 | 179.02 | 327.34 |
| 9 | 4.400 | .120 | 238.33 | 397.89 |
| 10 | 6.000 | .120 | 317.32 | 491.39 |
| 11 | 8.000 | .120 | 415.93 | 607.68 |
| 12 | 11.200 | .120 | 573.42 | 792.85 |
| 13 | 16.000 | .120 | 809.21 | 1069.47 |
| 14 | 23.200 | .120 | 1163.34 | 1485.54 |
| 15 | 32.000 | .120 | 1612.21 | 2075.77 |
| 16 | 60.000 | .120 | 2977.52 | 3152.36 |
| 1 | .000 | .160 | 28.54 | 169.50 |
| 2 | .200 | .160 | 38.05 | 181.75 |
| 3 | .400 | .160 | 47.67 | 194.02 |
| 4 | .800 | .160 | 67.09 | 218.49 |
| 5 | 1.200 | .160 | 86.68 | 242.77 |
| 6 | 1.800 | .160 | 116.20 | 278.85 |
| 7 | 2.400 | .160 | 145.80 | 314.60 |
| 8 | 3.200 | .160 | 185.33 | 361.90 |
| 9 | 4.400 | .160 | 244.67 | 432.28 |
| 10 | 6.000 | .160 | 323.75 | 525.42 |
| 11 | 8.000 | .160 | 422.47 | 641.14 |
| 12 | 11.200 | .160 | 580.12 | 825.27 |
| 13 | 16.000 | .160 | 816.11 | 1100.29 |
| 14 | 23.200 | .160 | 1170.42 | 1514.65 |

TABLE I-continued

| I | Boron | Iron | HI | LO |
|---|---|---|---|---|
| 15 | 32.000 | .160 | 1619.96 | 2113.65 |
| 16 | 60.000 | .160 | 2978.71 | 3153.22 |
| 1 | .000 | .220 | 38.79 | 216.91 |
| 2 | .200 | .220 | 48.23 | 228.94 |
| 3 | .400 | .220 | 57.77 | 241.06 |
| 4 | .800 | .220 | 77.04 | 265.35 |
| 5 | 1.200 | .220 | 96.48 | 289.54 |
| 6 | 1.800 | .220 | 125.83 | 325.56 |
| 7 | 2.400 | .220 | 155.32 | 361.28 |
| 8 | 3.200 | .220 | 194.77 | 408.52 |
| 9 | 4.400 | .220 | 254.07 | 478.73 |
| 10 | 6.000 | .220 | 333.18 | 571.53 |
| 11 | 8.000 | .220 | 432.00 | 686.66 |
| 12 | 11.200 | .220 | 589.84 | 869.70 |
| 13 | 16.000 | .220 | 826.07 | 1143.03 |
| 14 | 23.200 | .220 | 1180.63 | 1555.88 |
| 15 | 32.000 | .220 | 1631.28 | 2171.51 |
| 16 | 60.000 | .220 | 2980.46 | 3154.46 |
| 1 | .000 | .300 | 52.22 | 273.37 |
| 2 | .200 | .300 | 61.61 | 285.22 |
| 3 | .400 | .300 | 71.08 | 297.17 |
| 4 | .800 | .300 | 90.21 | 321.19 |
| 5 | 1.200 | .300 | 109.51 | 345.20 |
| 6 | 1.800 | .300 | 138.67 | 381.05 |
| 7 | 2.400 | .300 | 168.02 | 416.65 |
| 8 | 3.200 | .300 | 207.33 | 463.76 |
| 9 | 4.400 | .300 | 266.51 | 533.79 |
| 10 | 6.000 | .300 | 345.57 | 626.28 |
| 11 | 8.000 | .300 | 444.42 | 740.93 |
| 12 | 11.200 | .300 | 602.38 | 923.02 |
| 13 | 16.000 | .300 | 838.84 | 1194.79 |
| 14 | 23.200 | .300 | 1193.71 | 1606.46 |
| 15 | 32.000 | .300 | 1647.02 | 2243.38 |
| 16 | 60.000 | .300 | 2982.72 | 3155.89 |
| 1 | .000 | .400 | 68.67 | 336.62 |
| 2 | .200 | .400 | 78.03 | 348.29 |
| 3 | .400 | .400 | 87.46 | 360.06 |
| 4 | .800 | .400 | 106.47 | 383.75 |
| 5 | 1.200 | .400 | 125.63 | 407.50 |
| 6 | 1.800 | .400 | 154.61 | 443.04 |
| 7 | 2.400 | .400 | 183.80 | 478.42 |
| 8 | 3.200 | .400 | 222.94 | 525.31 |
| 9 | 4.400 | .400 | 281.93 | 595.07 |
| 10 | 6.000 | .400 | 360.85 | 687.25 |
| 11 | 8.000 | .400 | 459.63 | 801.49 |
| 12 | 11.200 | .400 | 617.63 | 982.84 |
| 13 | 16.000 | .400 | 854.25 | 1253.49 |
| 14 | 23.200 | .400 | 1209.44 | 1666.06 |
| 15 | 32.000 | .400 | 1665.91 | 2326.79 |
| 16 | 60.000 | .400 | 2985.44 | 3157.38 |
| 1 | .000 | .560 | 94.31 | 427.04 |
| 2 | .200 | .560 | 103.64 | 438.46 |
| 3 | .400 | .560 | 113.00 | 449.98 |
| 4 | .800 | .560 | 131.88 | 473.17 |
| 5 | 1.200 | .560 | 150.91 | 496.46 |
| 6 | 1.800 | .560 | 179.68 | 531.44 |
| 7 | 2.400 | .560 | 208.67 | 566.38 |
| 8 | 3.200 | .560 | 247.56 | 612.80 |
| 9 | 4.400 | .560 | 306.24 | 682.05 |
| 10 | 6.000 | .560 | 384.86 | 773.72 |
| 11 | 8.000 | .560 | 483.43 | 887.43 |
| 12 | 11.200 | .560 | 641.32 | 1068.04 |
| 13 | 16.000 | .560 | 878.00 | 1337.80 |
| 14 | 23.200 | .560 | 1233.67 | 1755.04 |
| 15 | 32.000 | .560 | 1694.78 | 2447.83 |
| 16 | 60.000 | .560 | 2989.63 | 3159.44 |
| 1 | .000 | .800 | 131.24 | 548.43 |
| 2 | .200 | .800 | 140.52 | 559.46 |
| 3 | .400 | .800 | 149.85 | 570.58 |
| 4 | .800 | .800 | 168.60 | 592.99 |
| 5 | 1.200 | .800 | 187.50 | 615.57 |
| 6 | 1.800 | .800 | 216.04 | 649.61 |
| 7 | 2.400 | .800 | 244.80 | 683.74 |
| 8 | 3.200 | .800 | 283.38 | 729.29 |
| 9 | 4.400 | .800 | 341.66 | 797.53 |
| 10 | 6.000 | .800 | 419.84 | 888.25 |
| 11 | 8.000 | .800 | 518.01 | 1001.14 |
| 12 | 11.200 | .800 | 675.52 | 1180.92 |
| 13 | 16.000 | .800 | 912.04 | 1450.51 |
| 14 | 23.200 | .800 | 1268.14 | 1884.98 |
| 15 | 32.000 | .800 | 1735.70 | 2597.43 |
| 16 | 60.000 | .800 | 2995.62 | 3161.82 |
| 1 | .000 | 1.160 | 183.50 | 716.24 |
| 2 | .200 | 1.160 | 192.73 | 726.48 |
| 3 | .400 | 1.160 | 202.00 | 736.83 |
| 4 | .800 | 1.160 | 220.63 | 757.77 |
| 5 | 1.200 | 1.160 | 239.38 | 778.98 |
| 6 | 1.800 | 1.160 | 267.68 | 811.19 |
| 7 | 2.400 | 1.160 | 296.17 | 843.75 |
| 8 | 3.200 | 1.160 | 334.40 | 887.51 |
| 9 | 4.400 | 1.160 | 392.17 | 953.64 |
| 10 | 6.000 | 1.160 | 469.76 | 1042.31 |
| 11 | 8.000 | 1.160 | 567.34 | 1153.51 |
| 12 | 11.200 | 1.160 | 724.20 | 1331.92 |
| 13 | 16.000 | 1.160 | 960.28 | 1602.78 |
| 14 | 23.200 | 1.160 | 1316.71 | 2086.27 |
| 15 | 32.000 | 1.160 | 1798.07 | 2765.64 |
| 16 | 60.000 | 1.160 | 3004.08 | 3164.29 |
| 1 | .000 | 1.600 | 243.71 | 909.74 |
| 2 | .200 | 1.600 | 252.52 | 922.80 |
| 3 | .400 | 1.600 | 261.35 | 935.84 |
| 4 | .800 | 1.600 | 279.61 | 956.17 |
| 5 | 1.200 | 1.600 | 298.21 | 974.46 |
| 6 | 1.800 | 1.600 | 326.28 | 1002.79 |
| 7 | 2.400 | 1.600 | 354.54 | 1032.03 |
| 8 | 3.200 | 1.600 | 392.44 | 1072.06 |
| 9 | 4.400 | 1.600 | 449.74 | 1133.78 |
| 10 | 6.000 | 1.600 | 526.74 | 1218.17 |
| 11 | 8.000 | 1.600 | 623.68 | 1325.92 |
| 12 | 11.200 | 1.600 | 779.79 | 1501.88 |
| 13 | 16.000 | 1.600 | 1015.27 | 1781.71 |
| 14 | 23.200 | 1.600 | 1372.43 | 2337.42 |
| 15 | 32.000 | 1.600 | 1871.08 | 2902.77 |
| 16 | 60.000 | 1.600 | 3013.57 | 3186.94 |
| 1 | .000 | 2.200 | 322.61 | 1135.91 |
| 2 | .200 | 2.200 | 331.41 | 1148.94 |
| 3 | .400 | 2.200 | 340.22 | 1161.95 |
| 4 | .800 | 2.200 | 357.87 | 1187.94 |
| 5 | 1.200 | 2.200 | 375.55 | 1213.93 |
| 6 | 1.800 | 2.200 | 402.14 | 1252.92 |
| 7 | 2.400 | 2.200 | 428.81 | 1291.84 |
| 8 | 3.200 | 2.200 | 464.79 | 1340.08 |
| 9 | 4.400 | 2.200 | 521.61 | 1387.57 |
| 10 | 6.000 | 2.200 | 598.01 | 1459.31 |
| 11 | 8.000 | 2.200 | 694.30 | 1557.61 |
| 12 | 11.200 | 2.200 | 849.62 | 1729.96 |
| 13 | 16.000 | 2.200 | 1084.47 | 2052.23 |
| 14 | 23.200 | 2.200 | 1443.10 | 2629.02 |
| 15 | 32.000 | 2.200 | 1969.69 | 3017.46 |
| 16 | 60.000 | 2.200 | 3024.96 | 3226.14 |
| 1 | .000 | 3.000 | 420.53 | 1411.63 |
| 2 | .200 | 3.000 | 429.30 | 1424.78 |
| 3 | .400 | 3.000 | 438.08 | 1437.92 |
| 4 | .800 | 3.000 | 455.65 | 1464.16 |
| 5 | 1.200 | 3.000 | 473.25 | 1490.38 |
| 6 | 1.800 | 3.000 | 499.69 | 1529.97 |
| 7 | 2.400 | 3.000 | 526.20 | 1569.79 |
| 8 | 3.200 | 3.000 | 561.62 | 1623.14 |
| 9 | 4.400 | 3.000 | 614.90 | 1705.14 |
| 10 | 6.000 | 3.000 | 686.20 | 1821.76 |
| 11 | 8.000 | 3.000 | 779.19 | 1933.49 |
| 12 | 11.200 | 3.000 | 933.86 | 2110.63 |
| 13 | 16.000 | 3.000 | 1168.41 | 2465.32 |
| 14 | 23.200 | 3.000 | 1530.52 | 2885.31 |
| 15 | 32.000 | 3.000 | 2093.85 | 3091.60 |
| 16 | 60.000 | 3.000 | 3032.78 | 3270.07 |
| 1 | .000 | 4.000 | 534.06 | 1738.23 |
| 2 | .200 | 4.000 | 542.78 | 1752.91 |
| 3 | .400 | 4.000 | 551.52 | 1767.58 |
| 4 | .800 | 4.000 | 569.00 | 1796.90 |
| 5 | 1.200 | 4.000 | 586.50 | 1826.19 |
| 6 | 1.800 | 4.000 | 612.79 | 1874.19 |
| 7 | 2.400 | 4.000 | 639.13 | 1923.37 |
| 8 | 3.200 | 4.000 | 674.32 | 1991.90 |

TABLE I-continued

| I | Boron | Iron | HI | LO |
|---|-------|------|------|------|
| 9 | 4.400 | 4.000 | 727.22 | 2103.11 |
| 10 | 6.000 | 4.000 | 797.98 | 2262.20 |
| 11 | 8.000 | 4.000 | 886.78 | 2459.59 |
| 12 | 11.200 | 4.000 | 1029.64 | 2725.83 |
| 13 | 16.000 | 4.000 | 1262.99 | 2871.10 |
| 14 | 23.200 | 4.000 | 1633.71 | 3047.23 |
| 15 | 32.000 | 4.000 | 2237.58 | 3140.90 |
| 16 | 60.000 | 4.000 | 3038.17 | 3315.80 |
| 1 | .000 | 6.000 | 740.89 | 2534.82 |
| 2 | .200 | 6.000 | 749.55 | 2553.15 |
| 3 | .400 | 6.000 | 758.21 | 2571.46 |
| 4 | .800 | 6.000 | 775.54 | 2604.16 |
| 5 | 1.200 | 6.000 | 792.89 | 2635.97 |
| 6 | 1.800 | 6.000 | 818.96 | 2683.64 |
| 7 | 2.400 | 6.000 | 845.07 | 2727.33 |
| 8 | 3.200 | 6.000 | 879.92 | 2781.16 |
| 9 | 4.400 | 6.000 | 932.33 | 2849.98 |
| 10 | 6.000 | 6.000 | 1002.40 | 2924.28 |
| 11 | 8.000 | 6.000 | 1090.44 | 2998.07 |
| 12 | 11.200 | 6.000 | 1232.43 | 3072.25 |
| 13 | 16.000 | 6.000 | 1449.99 | 3132.05 |
| 14 | 23.200 | 6.000 | 1838.22 | 3154.41 |
| 15 | 32.000 | 6.000 | 2472.50 | 3163.30 |
| 16 | 60.000 | 6.000 | 3045.57 | 3388.37 |

Other embodiments are within the following claims:

We claim:

1. An X-ray inspection device for detecting a specific material of interest in items of baggage or packages, comprising:

a conveyor constructed and arranged to move items of baggage or packages to an inspection region;

an X-ray source system located at said inspection region and constructed to expose an examined item of baggage or package by a beam of X-ray radiation;

an X-ray detection system located at said inspection region and constructed to detect X-ray radiation modified by said examined item;

a dimension detector constructed to measure a selected dimension of said examined item;

an interface system connected to and receiving from said X-ray detection system X-ray data and from said dimension detector dimension data, said interface system constructed to order said X-ray data and said dimension data;

a computer operatively connected to and receiving from said interface system said ordered X-ray and dimension data, said computer programmed to identify, based on said ordered X-ray and dimension data, a region of said item emitting scattered radiation characteristic of said specific material of interest in said examined item.

2. The device of claim 1 wherein said X-ray detection system includes an array of X-ray forward-scatter detectors constructed and positioned to detect X-ray radiation forward-scattered from said examined item to obtain X-ray forward-scatter data, and said computer being further programmed to estimate density of a material located in said identified region.

3. The device of claim 1 wherein said X-ray source system is further constructed to emit X-ray radiation of at least two substantially different energies, said X-ray detection system being further constructed to detect separately X-ray radiation, of two substantially different energies and modified by said examined item, and said computer being further programmed to identify said regions based on a ratio of scattered radiation at said two energies.

* * * * *